United States Patent [19]

Vandermeeren et al.

[11] Patent Number: 5,861,257
[45] Date of Patent: Jan. 19, 1999

[54] MONOCLONAL ANTIBODIES DIRECTED AGAINST THE MICROTUBULE-ASSOCIATED PROTEIN TAU, HYBRIDOMAS SECRETING THESE ANTIBODIES, ANTIGEN RECOGNITION BY THESE MONOCLONAL ANTIBODIES AND THEIR APPLICATIONS

[75] Inventors: Marc Vandermeeren, Geel, Belgium; Marc Mercken, Tokyo, Japan; Eugeen Vanmechelen, Nazareth-Eke; André Van De Voorde, Lokeren, both of Belgium

[73] Assignee: N.V. Innogenetics S.A., Belgium

[21] Appl. No.: 389,011

[22] Filed: Feb. 15, 1995

Related U.S. Application Data

[63] Continuation of Ser. No. 403,917, Jan. 19, 1995, which is a continuation-in-part of Ser. No. 403,916, Jan. 19, 1995, abandoned, which is a continuation-in-part of Ser. No. 244,951, Jun. 13, 1994 which is a continuation-in-part of PCT/NL93/03499 filed Dec. 10, 1993.

[30] Foreign Application Priority Data

Dec. 14, 1992 [EP] European Pat. Off. .............. 92403403

[51] Int. Cl.[6] .................................................. G01N 33/53
[52] U.S. Cl. .......................... 435/7.1; 435/7.21; 435/7.92; 435/7.95; 436/518; 436/63; 436/811
[58] Field of Search ..................................... 435/7.1, 7.21, 435/79, 7.92, 975; 530/300, 387.1, 387.9, 388.1, 389.1; 436/518, 63, 811

[56] References Cited

U.S. PATENT DOCUMENTS 5,492,812  2/1996  Vooheis.

OTHER PUBLICATIONS

Goedert et al, The EMBO Journal Article.vol. 8 pp. 393–399 1989.

Papasozomenos et al, Proc. Natl. Acad. Sci. USA Article vol. 88 May 1991 pp. 4543–4547 Biochemistry.

Yen et al, Am J. Pathol, 126:81–91, 1987.

Novak et al, Proc. Natl. Acad. Sci 88:5837–5841, 1991.

Mercken et al, Journal of Neurochemistry, 58:548–553, 1992.

*Primary Examiner*—Patricia Duffy
*Attorney, Agent, or Firm*—Bierman, Muserlian and Lucas

[57] ABSTRACT

The invention relates to a monoclonal antibody which forms an immunological complex with an epitope of an antigen belonging to normal human tau protein as well as abnormally phosphorylated human tau protein, with said tau protein being liable to be obtained from a brain homogenate, itself isolated from human cerebral cortex. The monoclonal antibodies of the invention can be used to detect tau and abnormally phosphorylated tau in brain extracts and in unconcentrated cerebrospinal fluid.

4 Claims, 7 Drawing Sheets

RGAA [PPGQK / HT7] GQANATRIPAKTPPAPKTPPSSGEPPKSGD [RSGYS / BT2][SPGSP / AT8] GTPGSRSRTPSLPTPPTR

FIG. 5

```
ATGGTAAGATCAAGTAGTCAAAATTCGAGTGACAAGCCTGTAGCCCACGTCGTAGCAAAC
 M   V   R   S   S   Q   N   S   S   D   K   P   V   A   H   V   V   A   N

CACCAAGTGGAGGAGCAGGGAATTCACCATCACCATCACCACGTGGATCCCGGGCCCATG
 H   Q   V   E   E   Q   G   I   H   H   H   H   H   V   D   P   G   P   M

GCTGAGCCCCGCCAGGAGTTCGAAGTGATGGAAGATCACGCTGGGACGTACGGGTTGGGG
 A   E   P   R   Q   E   F   E   V   M   E   D   H   A   G   T   Y   G   L   G

GACAGGAAAGATCAGGGGGGCTACACCATGCACCAAGACCAAGAGGGTGACACGGACGCT
 D   R   K   D   Q   G   G   Y   T   M   H   Q   D   Q   E   G   D   T   D   A

GGCCTGAAAGCTGAAGAAGCAGGCATTGGAGACACCCCCAGCCTGGAAGACGAAGCTGCT
 G   L   K   A   E   E   A   G   I   G   D   T   P   S   L   E   D   E   A   A

GGTCACGTGACCCAAGCTCGCATGGTCAGTAAAAGCAAAGACGGGACTGGAAGCGATGAC
 G   H   V   T   Q   A   R   M   V   S   K   S   K   D   G   T   G   S   D   D

SacII
AAAAAAGCCAAGGGGGCTGATGGTAAAACGAAGATCGCCACACCGCGGGGAGCAGCCCCT
 K   K   A   K   G   A   D   G   K   T   K   I   A   T   P   R   G   A   A   P

CCAGGCCAGAAGGGCCAGGCCAACGCCACCAGGATTCCAGCAAAAACCCCGCCCGCTCCA
 P   G   Q   K   G   Q   A   N   A   T   R   I   P   A   K   T   P   P   A   P

AAGACACCACCCAGCTCTGGTGAACCTCCAAAATCAGGGGATCGCAGCGGCTACAGCAGC
 K   T   P   P   S   S   G   E   P   P   K   S   G   D   R   S   G   Y   S   S

CCCGGCTCCCCAGGCACTCCCGGCAGCCGCTCCCGCACCCCGTCCCTTCCAACCCCACCC
 P   G   S   P   G   T   P   G   S   R   S   R   T   P   S   L   P   T   P   P

XmaI
ACCCGGGAGCCCAAGAAGGTGGCAGTGGTCCGTACTCCACCCAAGTCGCCGTCTTCCGCC
 T   R   E   P   K   K   V   A   V   V   R   T   P   P   K   S   P   S   S   A

PstI
AAGAGCCGCCTGCAGACAGCCCCCGTGCCCATGCCAGACCTGAAGAATGTCAAGTCCAAG
 K   S   R   L   Q   T   A   P   V   P   M   P   D   L   K   N   V   K   S   K

ATCGGCTCCACTGAGAACCTGAAGCACCAGCCGGGAGGCGGGAAGGTGCAAATAGTCTAC
 I   G   S   T   E   N   L   K   H   Q   P   G   G   G   K   V   Q   I   V   Y

AAACCAGTTGACCTGAGCAAGGTGACCTCCAAGTGTGGCTCATTAGGCAACATCCATCAT
 K   P   V   D   L   S   K   V   T   S   K   C   G   S   L   G   N   I   H   H

AAACCAGGAGGTGGCCAGGTGGAAGTAAAATCTGAGAAGCTTGACTTCAAGGACAGAGTC
 K   P   G   G   G   Q   V   E   V   K   S   E   K   L   D   F   K   D   R   V
```

FIG. 6A

```
CAGTCGAAGATTGGGTCCCTGGACAATATCACCCACGTCCCTGGCGGAGGAAATAAAAAG
 Q   S   K   I   G   S   L   D   N   I   T   H   V   P   G   G   G   N   K   K

ATTGAAACCCACAAGCTGACCTTCCGCGAGAACGCCAAAGCCAAGACAGACCACGGGGCG
 I   E   T   H   K   L   T   F   R   E   N   A   K   A   K   T   D   H   G   A

GAGATCGTGTACAAGTCGCCAGTGGTGTCTGGGGACACGTCTCCACGGCATCTCAGCAAT
 E   I   V   Y   K   S   P   V   V   S   G   D   T   S   P   R   H   L   S   N

GTCTCCTCCACCGGCAGCATCGACATGGTAGACTCGCCCCAGCTCGCCACGCTAGCTGAC
 V   S   S   T   G   S   I   D   M   V   D   S   P   Q   L   A   T   L   A   D

GAGGTGTCTGCCTCCCTGGCCAAGCAGGGTTTG
 E   V   S   A   S   L   A   K   Q   G   L
```

FIG. 6B

MONOCLONAL ANTIBODIES DIRECTED AGAINST THE MICROTUBULE-ASSOCIATED PROTEIN TAU, HYBRIDOMAS SECRETING THESE ANTIBODIES, ANTIGEN RECOGNITION BY THESE MONOCLONAL ANTIBODIES AND THEIR APPLICATIONS

PRIOR APPLICATIONS

This application is a continuation of U.S. patent application Ser. No. 08/403,917 filed Jan. 19, 1995, which is a continuation-in-part of U.S. patent application Ser. No. 08/403,916, filed Jan. 19, 1995, now abandoned which is a continuation-in-part of U.S. patent application Ser. No. 08/244,951, filed Jun. 13, 1994, which is a continuation-in-part of PCT application Ser. No. 93003499, filed Dec. 10, 1993.

The invention relates to new monoclonal antibodies directed against the human microtubule-associated protein tau, to the hybridomas secreting these monoclonal antibodies, and to the antigen recognition by these monoclonal antibodies and their applications. The invention also relates to a process for diagnosing brain diseases involving the particular epitope (of the tau protein) which is recognized by said monoclonal antibodies.

Alzheimer's disease (AD) is the most common form of adult-onset dementia. At present, no biochemical test is available for antemortem diagnosis of AD. The disease is therefore clinically diagnosed primarily by exclusion of other forms of dementia. The illness is characterized neuropathologically by the presence of neuritic (senile) plaques and neurofibrillary tangles (NFT).

Neurofibrillary tangles consist of paired helical filaments (PHF), of which the main protein component is a modified form of the microtubule-associated protein tau (Brion et al., 1985; Greenberg and Davies, 1990; Lee et al.,1991), which under normal circumstances promotes microtubule assembly and stability (Weingarten et al., 1975; Bré and Karsenti, 1990), which is synthesized in the neurons of several species, including humans (Kosik et al., 1989) and which is abundantly present in the axonal compartment of these neurons (Binder et al., 1985).

The protein exists as a family of different isoforms of which 4 to 6 isoforms are found in normal adult brain but only 1 isoform is detected in fetal brain (Goedert et al., 1989). The diversity of the isoforms is generated from a single gene by alternative mRNA splicing (Himmler, 1989). The most striking feature of tau protein, as predicted from molecular cloning, is a stretch of 31 or 32 amino acids occurring in the carboxy-terminal part of the molecule that is repeated 3 or 4 times. Additional diversity is generated through 29 or 58 amino acid-long insertions in the $NH_2$-terminal part of the molecules (Goedert et al., 1989).

Tau variants of 64 and 69 kDa, which are abnormally phosphorylated, as revealed by the (apparent increase in their molecular mass observed alter alkaline phosphatase treatment, have been detected exclusively in brain areas showing neurofibrillary tangles and senile plaques (Flament et al., 1989, 1990). The sites of phosphorylation by 4 different kinases have been mapped in the C-terminal microtubule-binding half of tau, and it could be shown that the action of a calcium calmodulin-dependent kinase on bacterially expressed tau resulted in the phosphorylation of Ser(405) which induced a lower electrophoretical mobility (Steiner et al., 1990). Tau present in paired helical filaments, called PHT-tau is abnormally phosphorylated (Lee et al., 1991). This abnormal phosphorylation causes a conformational change in tau, resulting probably in self-association and the formation of PHFs. PHF-tau in AD is phosphorylated at several sites, one of which is the phosphoserine 199 and/or 202. This site is specifically recognized by a mAb called AT8 (Biernat et al., 1992). Therefore, AT8 is a discriminative marker for PHF-tau (Goedert et al., 1992).

Several antibodies have been reported that show reactivity to human tau either because they are directed to non-specific phosphorylated epitopes present on neurofilament and subsequently shown to cross-react with normal and abnormally phosphorylated tau (Nukina et al., 1987; Ksiezak-Reding et al., 1987) or because they recognized specific epitopes on normal and abnormally phosphorylated tau (Kosik et al., 1988). In addition to the tau antibodies directed towards non-specific epitopes, antibodies directed specifically to phosphorylated tau epitopes have been described (Mercken et al., 1992b).

Although overall tau mRNA levels are only slightly modulated in Alzheimer-affected brain regions (Goedlert et al., 1988; Barton et al., 1990) it has been shown that total tau protein levels may differ at least 6-fold (Khatoon et al., 1992). This has been demonstrated by polygonal antibodies against tau (Flament and Delacourte, 1990) and by monoclonal antibodies directed to well-defined epitopes. The Alz 50 monoclonal antibody recognizing a phosphate-independent epitope in the N-terminus of the tau molecule (Goedert et al., 1991) has been used in a sandwich immunoassay on brain homogenates and it has been shown that taul levels are higher in Alzheimer's patient brains (Ghanbari et al., 1990; patent application EP 444 856).

An antibody named "423", raised against pronase-treated PHFs and specifically reactive with a 9.5 kDa and a 12 kDa fragment was also used to measure tau protein in Alzheimer's disease (patent application WO 89/03993). Similarly, it was found that increased mAb 423 immnunoreactivity was observed in Alzheimer brain homogenates as compared with control brain homogenates.

Mercken et al, (1992b) describe a range of monoclonal antibodies which are either specific for a phosphatase-sensitive epitope (AT8) or which react with PHF-tau as well as with normal tau (AT1, AT4, AT6, AT9, AT11, AT12 and AT14) in Western blotting.

Moreover, the antibody tau 1 (Wischik et al., 1988; Harrington et al., 1990) was also used to measure tau in brain homogenates. In one case when tau levels were specifically measured in Alzheimer-affected brain sections, tau levels were eight-fold higher as compared with levels in normal brain homogenates (Khatoon et al., 1992).

In a first attempt to diagnose Alzheimer disease in cerebrospinal fluid, the PHF-tau-specific monoclonal antibody AT8 (Mercken et al., 1992b), was used. However, no PHF tau antigen could be demonstrated.

Thus far, none of the monoclonals that have been described have been successful in detecting tau in non-concentrated cerebrospinal fluid (CSF), although the presence of tau was observed in 100-fold concentrated CSF (Wolozin and Davies, 1987) or in CSF samples using polyclonal antibodies (Delacourte and Vermersch, 1991).

The aim of the present invention is therefore to provide monoclonal antibodies which allow reliable and sensitive detection of normal and abnormally phosphorylated tau present in brain extracts and in unconcentrated cerebrospinal fluid. The invention also aims at providing the hybridoma which secretes the above-said monoclonal antibodies.

The invention furthermore aims at providing the epitope of the tau protein present in brain homogenates or in body fluids such as cerebrospinal fluid, which is recognized by said monoclonal antibodies.

The invention aims at providing a process for the detection or diagnosis in vitro of brain diseases involving tau protein.

The monoclonal antibodies of the invention are characterized by the fact that they react with an epitope which is present in both normal and abnormally phosphorylated human tau protein. The monoclonal antibodies are furthermore characterized by the fact that they form an immunological complex with an epitope or an antigen belonging to normal and abnormally phosphorylated human tau protein. The monoclonal antibodies of the invention are also characterized by the fact that they do not form an immunological complex with other phosphorylated proteins such as MAP-1, MAP-2 and neurofilaments which share part of their sequence with tau protein (Nukina et al., 1987; Lewis et al., 1988) as determined by means of an ELISA. The monoclonal antibodies of the invention are also characterized by the fact that they are liable to detect human tau protein in CSF, with said tau protein being at a concentration as low as 1.0 pg/ml and with said tau protein being detected at 100% recovery upon the addition of a fixed amount of tau protein in tau protein-negative CSF (100% spiking recovery).

The monoclonal antibodies of the invention also enable the diagnosis of Alzheimer's disease (AD) on the basis of CSF, i.e., to detect tau and modified forms of tau in CSF. The problem associated herewith is that this antigen is present in a very low amount in CSF, therefore the detection assay must be very sensitive. This problem can be resolved by using the combination of the monoclonal antibody of the invention together with the catalysed reporter deposition amplification technique (CARD, Bobrow et al., 1989), allowing a tau-specific CARD ELISA with a higher sensitivity. Alternatively, a mixture or combinations of labeled monoclonal antibodies, each recognizing epitopes different from AT120 epitope, could be used as detector antibodies.

The results obtained with the monoclonal antibody secreted by the hybridoma AT120 of the invention indicate that elevated tau levels are not only found in AD, but also in other neurological diseases where neuronal death or damage occurs.

The expression "form an immunologically complex with" means that the monoclonal antibody of the invention binds to the above-said antigen under one of the following conditions as mentioned in the techniques below:

Light Immunomicroscopy

Brain tissue samples, obtained at surgery or autopsy, are fixed by immersion in 4% formalin or Bouin's fixative and embedded in paraffin for sectioning. The monoclonal antibodies of the invention are applied in conjunction with a technique to visualize the formed immune complexes such as the avidin-biotinylated peroxidase complex technique (Hsu et al., 1981) using 3,3'-diaminobenzidine tetrahydrochloride for development of color. Sections are counterstained with Harris haematoxylin stain.

Immunoelectron Microscopy in Tissue Sections

Brain tissue samples, obtained at surgery or autopsy are fixed in either Bouin's fixative or 10% buffered formalin before sectioning without embedding (Vibratome). The monoclonal antibody of the invention is used for immunostaining by the indirect immunogold method after which the sections are fixed, embedded and sectioned for electron microscopy, all according to standard protocols known to those skilled in the art (Brion et al., 1985).

Immunoblotting Procedures

For immunoblotting, fractions enriched in tau are prepared as described (Lindwall and Cole, 1984). Typically, 50 g of brain tissue is cut into small pieces with scissors and homogenized 1:1 (wt/vol) in buffer A (20 mM 2-[N-morpholino]ethanesulfonic acid, 80 mM NaCl, 2 mM EDTA, 0.1 mM EGTA, 1 mM β-mercaptoethanol, pH 6.75) with a Potter homogenizer equipped with a Teflon plunger. The homogenate is centrifuged for 1 h at 150,000 g at 4° C., and the supernatant is heated for 5 min in boiling water and chilled again for 10 min on ice. The slurry is centrifuged for 2 h at 150,000 g at 4° C., and the supernatant is collected. The heat-stable cytosolic extract is added to 2.5% perchloric acid and centrifuged for 1at 150,000 g at 4° C., after which the supernatant is neutralized with 3M Tris. The supernatant is then dialyzed in water and concentrated in a Centriprep concentrator (Amicon, Lausanne, Switzerland).

SDS-polyacrylamide electrophoresis is performed under reducing conditions on 12% gels (Laemmli, 1970). After electrophoresis, the proteins are either fixed and stained with Coomnassie brilliant blue, or transferred (Towbin et al., 1979) to nitrocellulose sheets (Hybond-C, Amersham) or Immobilon filters (Millipore).

After transfer, the filters are presoaked in PBS containing 0.05% (v/v) Tween 20 (Tween-PBS) and then incubated for 1 h in Tween-PBS containing 5% (w/v) skimmed dried milk and 10% (v/v) newborn calf serum (blocking buffer). Next, the filters are treated overnight at 4° C. with a monoclonal antibody according to the invention appropriately diluted in blocking buffer.

The filters are then washed three times in Tween-PBS and treated for 1.5 h at room temperature with horseradish peroxidase-labeled rabbit anti-mouse IgG (Dakopatts, Denmark) diluted $\frac{1}{3000}$ in blocking buffer. After three washes in Tween-PBS, streptavidine-biotinylated horseradish peroxidase complex (Amersham), diluted $\frac{1}{250}$ in blocking buffer, is applied for 1.5 h at room temperature. Thereafter, the filters are washed three times in Tween-PBS and once in PBS. The filters are then incubated in PBS containing 0.05% (w/v) diaminobenzidine and 0.03% (v/v) hydrogen peroxide until background staining develops.

It should be clear that the formation of an immunological complex between the monoclonal antibodies and the antigen is not limited to the precise conditions described above, but that all techniques that respect the immunochemical properties of the antibody and antigen binding will produce similar formation of an immunological complex.

Human normal tau is a class of at least six tau proteins ranging in molecular weight from 58 to 64 kDa which are specifically expressed in the somatodendritic domain of all neurons (Papasozomenos and Binder, 1987). Moreover Alzheimer (tangle)-specific tau forms have been described which occur in the degenerating cortical neurons of Alzheimer's disease or Down's Syndrome and of which the lower electrophoretic mobility can be attributed to abnormal phosphorylation (Flament et al., 1989; Delacourte et al., 1990).

According to an advantageous embodiment of the invention, the monoclonal antibody forms an immunological complex with all forms of tau described above, with said human tau protein being liable to be obtained from a brain homogenate, itself isolated from the cerebral cortex of a patient suffering from a neurological disease.

A "brain homogenate" and tau protein can be obtained by the man skilled in the art according to standard methods such as the method of Lindwall and Cole (1984).

According to an advantageous embodiment, the monoclonal antibodies of the invention form an immunological complex:

either with an epitope located within the following amino acid sequence of human tau protein:

```
       155                         160                         165
NH₂—Arg  Gly  Ala  Ala  Pro  Pro  Gly  Gln  Lys  Gly  Gln  Ala  Asn  Ala
       170                         175                         180
    Thr  Arg  Ile  Pro  Ala  Lys  Thr  Pro  Pro  Ala  Pro  Lys  Thr  Pro  Pro
         185                         190                         195
         Ser  Ser  Gly  Glu  Pro  Pro  Lys  Ser  Gly  Asp  Arg  Ser  Gly  Tyr  Ser
         200                         205                         210
    Ser  Pro  Gly  Ser  Pro  Gly  Thr  Pro  Gly  Ser  Arg  Ser  Arg  Thr  Pro
         215                         220
    Ser  Leu  Pro  Thr  Pro  Pro  Thr  Arg  (SEQ ID NO 1)
``` more specifically with an epitope located within the following amino acid sequence:

```
199  200                         205                         210
Ser  Pro  Gly  Ser  Pro  Gly  Thr  Pro  Gly  Ser  Arg  Ser  Arg  Thr  Pro
     215                         220                         225
Ser  Leu  Pro  Thr  Pro  Pro  Thr  Arg  Glu  Pro  Lys  Lys  Val  Ala  Val
     230  231
Val  Arg  Thr  (SEQ ID NO 2)
``` more specifically with an epitope located within the following amino acid sequence:

```
207            210                 215
Gly  Ser  Arg  Ser  Arg  Thr  Pro  Ser  Leu  Pro  Thr  Pro  Pro
(SEQ ID NO 3)
``` most specifically with an epitope located within the following amino acid sequence:

```
218                      224
Pro  Pro  Thr  Arg  Glu  Pro  Lys
(SEQ ID NO 4)
``` or with any other peptide capable of forming an immunological complex with a monoclonal antibody, which is capable of forming a complex with an epitope located in a tau protein regions as shown in any of SEQ ID NO 1 to 4.

The sequences as shown in SEQ ID NO 1 to 4 will be hereafter designated as containing "the epitope" of the invention. Amino acid sequence 1 spans the amino acids 155–221 of human tau using the numbering of human tau 40, amino acid sequence 2 spans the amino acids 199–231 of human tau, amino acid sequence 3 spans the amino acids 207–219 of human tau, and amino acid sequence 4 spans the amino acids 218–224 of human tau (Goedert et al., 1989).

The peptides capable of forming an immunological complex with a monoclonal antibody, which itself is liable to form a complex with the above-mentioned peptide will be defined as the "variant peptides".

A preferred monoclonal antibody of the invention is secreted by the hybridoma deposited at ECACC (European Collection of Animal Cell Cultures, Vaccine Research and Production Laboratory, Public Health and Laboratory Service (PHLS), Centre for Applied Microbiology and Research, Proton Down, GB-Salisbury, Wiltshire SP4 OJG) on Oct. 8, 1992 under No. 92100853.

This hybridoma will be hereafter designated as "hybridoma AT120" and the secreted monoclonal antibody will be designated as "monoclonal antibody AT120".

The invention also relates to the hybridoma which secretes a monoclonal antibody according to the invention, and particularly the hybridoma filed at ECACC on Oct. 8, 1992 under No. 92100853.

The above-mentioned monoclonal antibodies are obtained by a process involving obtention and isolation of hybridomas which secrete these monoclonal antibodies.

A process for obtaining the hybridoma involves:
  starting from spleen cells of an animal, e.g. mouse or rat, previously immunized in vivo, or from spleen cells of such cells previously immunized in vitro with an antigen recognized by the monoclonal antibody deposited at ECACC on Oct. 8, 1992 under No. 92100853, or with a peptide containing or which are constituted by parts of any of the sequences as represented in SEQ ID NO 1 to 4;
  fusing said immunized cells with myeloma cells under hybridoma-forming conditions; and
  selecting those hybridomas which secrete the monoclonal antibodies which specifically recognize an epitope of the above-said antigen and which form an immunological complex with normal tau or the abnormally phosphorylated form of tau protein or with the peptide comprising the epitope of tau recognized by the monoclonal antibody of the invention.

A process for producing the corresponding monoclonal antibodies involves:
  culturing the selected hybridoma as indicated above in an appropriate culture medium; and
  recovering the monoclonal antibodies secreted by said selected hybridoma; or alternatively
  implanting the selected hybridoma into the peritoneum of a mouse and, when ascites has been produced in the animal;
  recovering the monoclonal antibodies then formed from said ascites.

The monoclonal antibodies of the invention can be prepared by conventional in vitro techniques such as the culturing of immobilized cells using e.g. hollow fibers or microcapsules or such as the culturing of cells in homogeneous suspension using e.g. airlift reactors or stirred bioreactors.

The invention also relates to a peptide (antigen), which can be obtained from a human brain homogenate itself being isolated from the human cerebral cortex obtained from a patient having Alzheimer's disease, and which forms an immunological complex with the monoclonal antibody of the invention.

The invention also relates to peptides (antigens) which are liable to form an immunological complex with anyone of the monoclonal antibodies of the invention and which are contained in or are constituted by parts of the sequence as shown in SEQ ID NO 1, 2, 3, or 4;

which contain or are constituted by the sequence of the variant peptides defined above.

It is to be recalled that variant peptides are those peptides able to form an immunological complex with a monoclonal antibody, which itself is liable to form a complex with an epitope located in the tau protein region as shown in SEQ ID NO 1 to 4.

The invention also relates to polypeptides (antigens) of about 100 amino acids which contain the sequence as shown in SEQ ID NO 1 to 4, or which contain the sequence of the variant peptides defined above.

The invention also relates to the above-mentioned peptides which are liable to generate monoclonal antibodies of the invention.

The invention also relates to a peptide (antigen) which is contained in the brain, in the cerebrospinal fluid, or in the serum of a patient having Alzheimer's disease or any brain disease involving normal human tau protein and which forms an immunological complex with a monoclonal antibody of the invention.

The invention also relates to a peptide (antigen) which is contained in the brain, in the cerebrospinal fluid, or in the serum of a patient having Alzheimer's disease or any brain disease involving PHF or abnormally phosphorylated human tau protein and which forms an immunological complex with a monoclonal antibody of the invention.

A method for preparing the peptides of the invention is characterized in that, preferably starting from the C-terminal amino acid, the successive aminoacyl in the requisite orders or aminoacyls and fragments formed beforehand and already containing several aminoacyl residues in the appropriate order, or alternatively several fragments prepared in this manner beforehand, are coupled successively in pairs, it being understood that care will be taken to protect all the reactive groups carried by these aminoacyls or fragments beforehand except for the amine groups of one and carboxyl groups of the other, or vice versa, which must normally participate in peptide bond formation, in particular after activation of the carboxyl group, according to methods known in peptide synthesis, and so on, proceeding stepwise up to the N-terminal amino acid.

The antigen of the invention, which can be prepared by methods known to those skilled in the art (Lindwall and Cole, 1984) starting from the human cerebral cortex is characterized by its ability to form an immunological complex with the monoclonal antibody of the invention as defined above, advantageously with the monoclonal antibody secreted by the hybridoma AT120 deposited at the ECACC under No. 92100853 on Oct. 8, 1992.

The antigen of the invention is advantageously contained in the brain, in the cerebrospinal fluid or the serum of a patient having Alzheimer's disease, Down syndrome, Pick's disease, subacute sclerosing panencephalitis (SSPE) or other neurological diseases in which the normal tau or abnormally phosphorylated tau protein are implicated; this antigen provokes an immunological reaction with the monoclonal antibody of the invention.

The invention also relates to a process for the detection or the diagnosis in vitro of brain disease involving tau protein, i.e. Alzheimer's disease, which involves:

bringing the monoclonal antibody of the invention into contact with a preparation of NFT containing tau protein or a detergent-extracted brain homogenate containing tau protein isolated from a patient having had Alzheimer's disease or any other disease involving tau protein or abnormally phosphorylated tau protein under conditions suitable for producing an antigen-antibody complex; and, separating the antigen from said complex and recovering the antigen sought in a purified form.

The preparation of tau can be carried out according to Lindwall and Cole (1984).

Advantageously, the monoclonal antibodies used are in an immobilized state on a suitable support such as a resin. The process for the detection of the antigen can then be carried out as follows:

bringing the supernatant containing proteins and polypeptides obtained as a result of an extraction procedure starting from brain tissues or cerebrospinal fluid known to those skilled in the art (Iqbal et al., 1984; Greenberg and Davies, 1990) into contact with said monoclonal antibody, under such conditions as to allow the formation of an immunological complex;

washing the immobilized antibody-antigen complex then formed;

treating this complex with a solution (e.g. 3M potassium thiocyanate, 2.5M magnesium chloride, 0.2M citrate-citric acid, pH 3.5 or 0.1M acetic acid) capable of producing the dissociation of the antigen-antibody complex; and;

recovering the antigen in a purified form.

The process of the invention for the detection or diagnosis in vitro of brain disease involving tau protein and abnormally phosphorylated tau protein, as e.g. in Alzheimer's disease, includes:

bringing a sample of a brain homogenate, or of cerebrospinal fluid, or of serum from a patient suspected of suffering from a neurological disorder involving tau protein or PHF, more particularly Alzheimer's disease, into contact under in vitro conditions with the monoclonal antibody of the invention, with said conditions being suitable for producing an antigen-antibody complex; and detecting the immunological binding of said antibody to said sample of brain homogeniate, or of cerebrospinal fluid, or of serum.

The detection of the immunologically bound monoclonal antibody can be achieved by conventional technology. Advantageously, the monoclonal antibody of the invention itself carries a marker or a group for direct or indirect coupling with a marker as exemplified hereafter. Also, a polyclonal antiserum can be used which was raised by injecting the antigen of the invention in an animal, preferably a rabbit, and recovering the antiserum by immunoaffinity purification in which said polyclonal antibody is passed over a column to which said antigen is bound and eluting said polyclonal antibodies by conventional technology.

Detection can also be achieved by competition binding of the antigen with a labeled peptide comprising the epitope of the invention.

A particularly advantageous embodiment of the process of the invention for the detection or diagnosis in vitro of brain diseases involving PHF and/or normal tau protein, e.g. Alzheimer's disease, comprises the steps of:

bringing a sample of unconcentrated cerebrospinal fluid sample isolated from a patient suspected of suffering from a neurological disorder involving normal or abnormally phosphorylated tau protein, more particulary Alzheimer's disease, into contact under in vitro conditions with a monoclonal antibody according to the invention, under conditions suitable for producing an antigen-antibody complex; and, detecting the immunological binding of said antibody to said sample of cerebrospinal fluid by means of a sandwich ELISA, preferably by applying the catalysed reporter diagnosis enhancement (CARD) procedure.

The invention also relates to a kit for the diagnosis in vitro of one of the following diseases: Alzheimer's disease, Down's syndrome, Pick's disease, subacute sclerosing panencephalitis (SSPE) and other neurodegenerative disorders in which normal tau protein or abnormally phosphorylated tau protein are implicated. Such a kit would contain:

at least one microplate for deposition thereon of any monoclonal antibody of the invention;

a preparation containing the sample to be diagnosed in vitro, possibly together with a labeled peptide containing the epitope of the invention and preferably, a peptide lying in the peptide sequence as shown in SEQ ID NO 1 to 4, a second antibody
which can be a monoclonal antibody recognizing another epitope of normal or abnormally phosphorylated tau protein, or of any peptide of the invention, with said epitope being different from the one of the invention, or which can be a polyclonal antibody directed against normal or abnormally phosphorylated tau, or against a peptide of the invention, with said polyclonal antibody being liable to form an immunological complex with epitopes which are all different from the epitope of the invention, with said polyclonal antibody being preferably purified by immunoaffinity chromatography using immobilized tau protein, or a marker either for specific tagging or coupling with said second antibody;

appropriate buffer solutions for carrying out the immunological reaction between the monoclonal antibody of the invention and a test sample on the one hand, and the bound second antibody and the marker on the other hand.

The labeled peptide mentioned above can be a peptide which has been labeled by any means known for the man skilled in the art. Moreover, the marker specific for tagging and coupling can be any marker known to the man skilled in the art.

The invention also relates to a kit, as described above, also containing the antigen of the invention, with said antigen of the invention being either a standard (for quantitative determination of the antigen which is sought) or a competitor, with respect to the antigen which is sought, for the kit to be used in a competition dosage process.

Western blotting detection of normal tau or PHF-tau using the monoclonal antibodies Tau-1, (Binder et al., 1985) AT8 (Mercken et al., 1992b) and AT120. Lanes 1, 3 and 5: PHF-tau isolated according to Greenberg and Davies (1990). Lanes 2, 4 and 6: Normal affinity purified human tau according to Mercken et al. (1992a). Lane 7: Molecular weight markers.

Lanes 1 and 2 were developed using AT8, lanes 3 and 4, using AT120 and lanes 5 and 6, using Tau-1 monoclonal antibody.

Figure 2A:
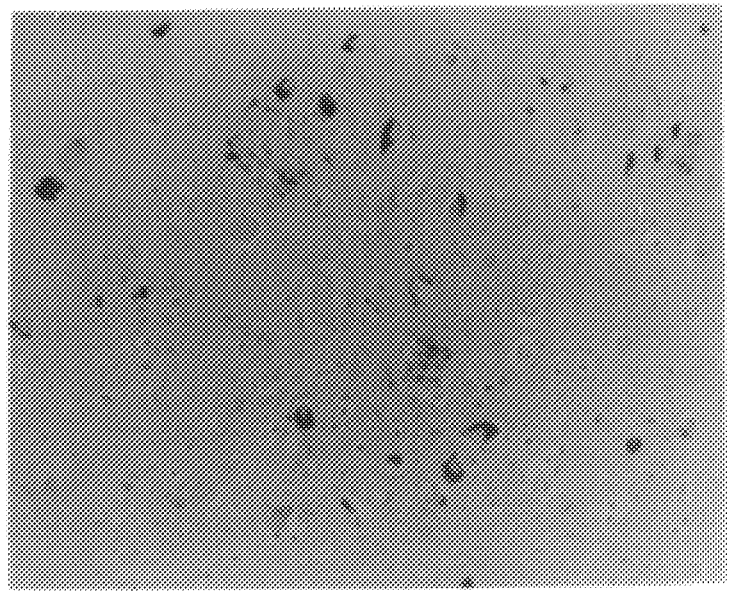
Figure 2B:
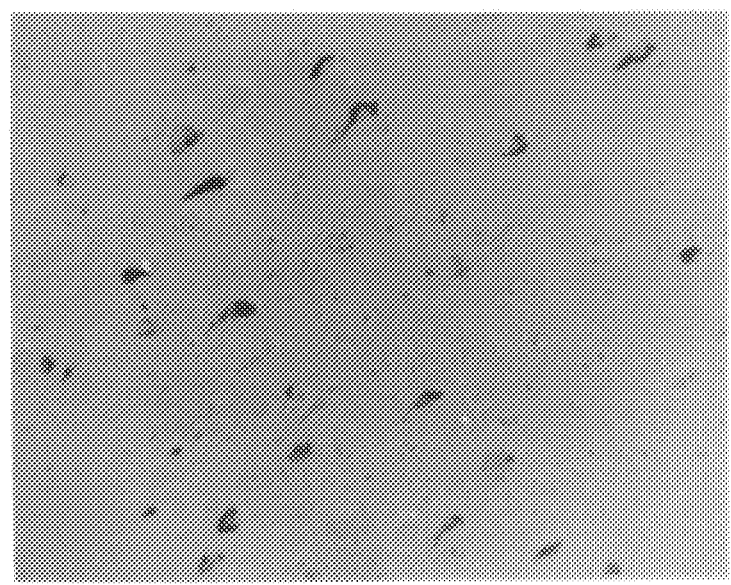

FIG. 2A and FIG. 2B

Detection of tau protein by immunochemistry

FIG. 2A: section from hippocampus of a patient with Alzheimer's disease. Magnification 212×.

FIG. 2B: section from another hippocampus of a patient with Alzheimer's disease with abundant tangles. Magnification 212×.

FIG. 3

Titration of normal (0) and PHF tau (■), spiked in a tau-negative CSF pool using the amplified (CARD) AT120 sandwich ELISA. All dilutions were tested in duplicate and the data presented as optical density (OD) units.

FIG. 4

Western blotting of several deletion mutants constructed as indicated in example V, and stained with AT120 as indicated in Example 1. Mutants comprise the following amino acids (AA); Lane 1, full length tau 34 (Goedert et al., 1989); Lane 2, amino terminus of tau 34 up to $AA_{154}$; Lane 3, from $AA_{155}$, to the carboxyterminus of tau 34; Lane 4; aminoterminus of tau 34 up to $AA_{242}$; Lane 5, aminoterminus tau 34 up to $AA_{222}$; Lane 6, from $AA_{222}$ to the carboxyterminus of tau 34.

FIG. 5

Epitope recognition sites of the monoclonal antibodies HT7, BT2, AT8 are depicted on the epitope of the invention (SEQ ID NO 1) shown in the one letter amino acid code. Epitopes are boxed. The star "*" designates the fact that the AT8 epitope recognition needs phosphorylation of serine residue 202.

FIG. 6A and 6B

Complete sequence of the mTHFMPH-tau 1 fusion protein (SEQ ID NO 23) with indication of relevant restriction sites on the nucleotide sequence (SEQ ID NO:25).

EXAMPLES

Example I

Preparation of the monoclonal antibody AT120 (IgG1, subtype kappa)

1. Preparation of the antigen for immunization

PHF-tau was partially purified by a modification of the method of Greenberg and Davies (1990). Postmortem tissue, consisting mostly of gray matter from the frontal and temporal cortex, was obtained from histologically confirmed Alzheimer patients. This Alzheimer gray matter brain sample (5–10 g) was homogenized with 10 volumes of cold buffer H (10 mM Tris/1 mM EGTA/0.8M NaCl/10% sucrose, pH 7.4) in a Teflon/glass Potter S (Braun, Germany) homogenizer. After centrifugation of the homogenate in a 60 Ti MSE rotor at 27,000×g for 20 min at 4° C., the pellet was removed and the supernatant was adjusted to 1% (wt/vol) N-laurosylsarcosine and 1% (vol/vol) 2-mercaptoethanol and incubated while rotating on a mixer (Swelab, Sweden) for 2.5 hours at 37° C. The supernatant mixture was centrifuged at 108,000×g for 35 min at 20° C. The PHF-tau containing pellet was gently washed with PBS and finally suspended in 1 ml of the same buffer.

The antigen preparation was evaluated by a 10% sodium dodecyl sulfate-polyacrylamide gel electrophoresis, followed by , Western blotting using immunoblotting with polyclonal rabbit antihuman normal tau antiserum (Mercken et al., 1992b).

2. Immunization protocol and fusion procedure

Balb/c mice were primed subcutaneously with 100 µg partially purified PHF-tau in complete Freund's adjuvant and boosted intraperitoneally 3 times thereafter at 3-week intervals with 100 µg of the same antigen in incomplete Freund's adjuvant. On days 3 and 2 before the fusion, mice were boosted with 100 µg PHF-tau in saline.

Mouse spleen cells were fused with SP2/0 myeloma cells, using a modified procedure of Köhler and Milstein (1975), with PEG 4000.

The cells of the fusion experiment were suspended at a density of $4.5 \times 10^4$ spleen cells/well on 96-well plates pre-seeded with mouse peritoneal macrophage cells as a feeder layer. These wells were screened after 12 days for anti-tau antibody production in a sandwich ELISA either specific for normal tau or for PHF-tau as discussed in section 3. below.

Hybridoma growth was in Dulbecco's modified Eagle's medium (DMEM) supplemented with 20% fetal calf serum, sodium pyruvate (1 mM), L-glutamine (2 mM), penicillin (100 U/ml), streptomycin (100 mg/ml), and nonessential amino acids. All products were purchased from Gibco, (Paisley, U.K.). Cells were incubated in a humidified $CO_2$-air incubator.

3. Sandwich ELISA for antibody screening

The screening ELISA used for the detection of anti-tau monoclonal antibodies was a sandwich ELISA system with affinity-purified polyclonal rabbit anti-human tau antibodies (Mercken et al; 1992a) in the coating phase. To this end, purified human normal tau, prepared as described in Mercken et al. (1992a) was used for the preparation of an immunoaffinity column using cyanogen bromide-activated Sepharose (Pharmacia, LKB Sweden). The affinity-bound anti-tau fraction was eluted from this column with a 0.1M citric acid buffered solution at pH 2.5. After neutralization, the anti-tau-containing fractions were pooled and coated overnight (1 µg/ml) at 4° C. on high-binding microtiter plates (Nunc, Gibco, Paisley, UK) in coating buffer (10 mM Tris, 10 mM NaCl, 10 mM $NaN_3$, pH 8.5). After overcoating for 30 min with 125 µl 0%-saturated casein in PBS to reduce non-specific binding, the plates were incubated with 100 µl of an appropriately diluted PHF-tau preparation and incubated for 60 min at 37° C. The plates were washed 3 times with PBS-0.05% Tween 20 (v/v); 100 µl hybridoma supernatant was added and incubation was continued for 1 h at 37° C. After washing, the bound monoclonal antibodies were detected with peroxidase-conjugated rabbit anti-mouse serum (Dakopatts, Glostrup, Denmark). All reagents were diluted in PBS with 10% casein. After final washing, 100 µl 0.42 mM 3,5,3',5'-tetramethylbenzidine, 0.003% $H_2O_2$ v/v in 100 mM citric acid, 100 mM disodium hydrogen phosphate, pH 4.3, was added as peroxidase substrate. The reaction was stopped with 50 µl of a 2M $H_2SO_4$ solution. Absorbance was read in a Titertek Multiscan (Flow Laboratories, Eflab, Oy, Finland) at 450 nm.

The cross-reactivity of the monoclonal antibodies with normal tau in ELISA was tested in a sandwich ELISA identical to the screening assay, except that affinity-purified normal tau was used as the antigen instead of PHF-tau.

At the first selection of positive hybridoma cultures, most positive cultures were initially composed of mixed clones as seen by visual inspection of the wells (3–4 clones per well). These positive cultures were arbitrarily designated AT1 to AT24 (some of these hybridoma cultures, i.e., AT1 to AT14 were described by Mercken et al, 1992b). After this initial screening round, hybridoma cultures were subcloned by limiting dilution, a technique well-know to those skilled in the art, finally resulting in pure hybridoma clones secreting antibodies with a homogeneous idiotype. These pure hybridoma clones were further tested with respect to their reactivity pattern on normal and PHF-tau in ELISA, Western blotting and immunohistochemistry, and to their capability to diagnose neurological diseases by means of their affinity for tau protein present in an undiluted sample of cerebrospinal fluid. Based on these criteria, the monoclonal antibody AT120 was selected and further characterized as shown in the following examples.

4. Determination of the antibody class and subclass

The antibody class and subclass was determined by Inno-LIA (Innogenetics, Ghent, Belgium). The antibody of the invention, AT120, appeared to be of the IgG1, kappa subtype.

Example II

Detection of pathological tau and normal tau in ELISA and by Western blotting

1. Detection of normal tau in ELISA using AT120.

Protein G-purified monoclonal antibody AT120, obtained from serum-free hybridoma AT120 conditioned medium, was coated on ELISA plates and reacted with different dilutions of affinity-purified human normal tau as described in Mercken et al. (1992a), prepared in a solution of PBS and 10% casein.

The purity of normal tau was determined by SDS-PAGE. Tau samples were analyzed on an 420 A/H amino acid analyzer (Applied Biosystems B.V., Maarssen, The Netherlands) according to the manufacturer's instructions and the protein showed the expected amino acid composition. From the amino acid composition and by comparison with a standard peptide the concentration of normal tau was determined.

Figure 3:
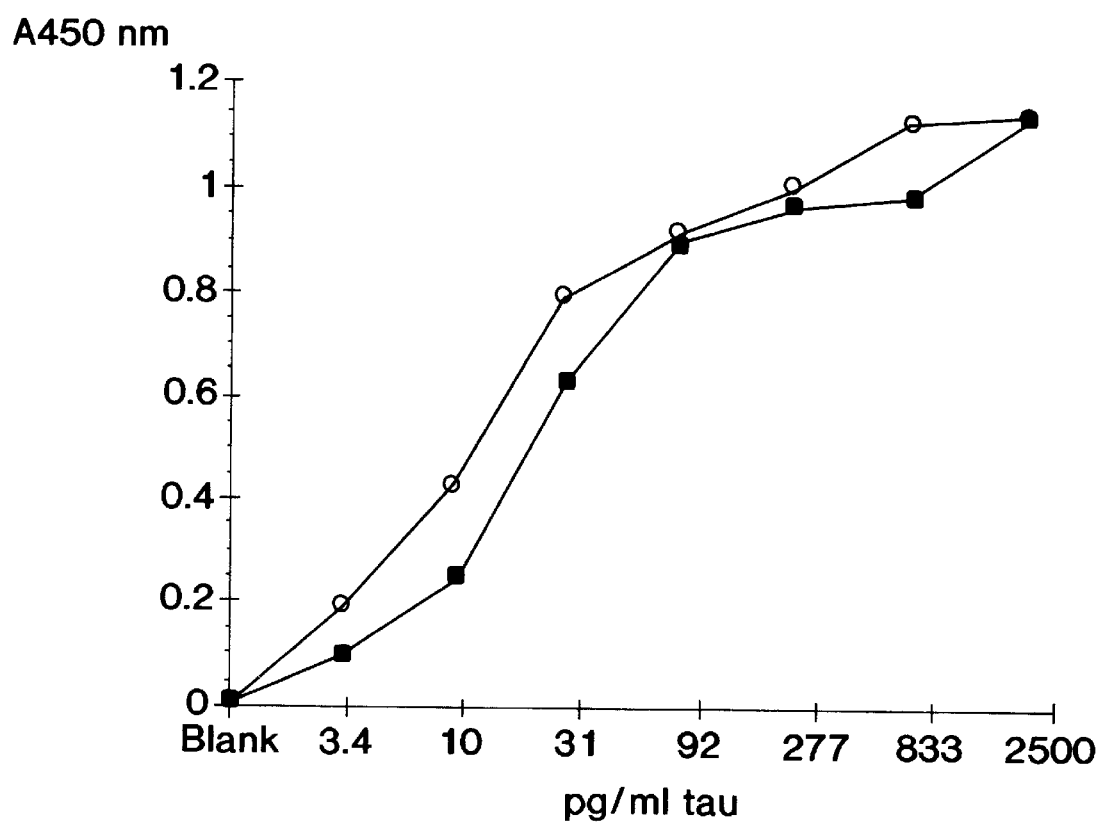

After incubation of the ELISA plates with different concentrations of tau spiked in tau- and PHF-tau-negative CSF for 1 h at room temperature, the plates were washed and incubated with 0,2 µg/ml biotinylated BT2 and HT7, each recognizing an epitope different from the AT120 epitope and present on normal term. After washing, complexed biotynilated antibodies were detected with horseradish peroxidase conjugated streptavidine (Jackson) and color development as specified in example I. The results are shown in Table I and FIG. 3.

TABLE 1

Detection of normal tau in ELISA

| CONCENTRATION | ABSORBANCE (expressed as milli-absorbance units) | |
|---|---|---|
| (pg/ml) | PHF-tau | normal tau |
| 160 | 1682 | 1609 |
| 80 | 901 | 970 |
| 40 | 566 | 678 |
| 20 | 257 | 256 |
| 10 | 143 | 154 |
| 0 | 92 | 87 |

2. Detection of pathological tau and of normal tau in Western blotting using AT120.

Figure 1:
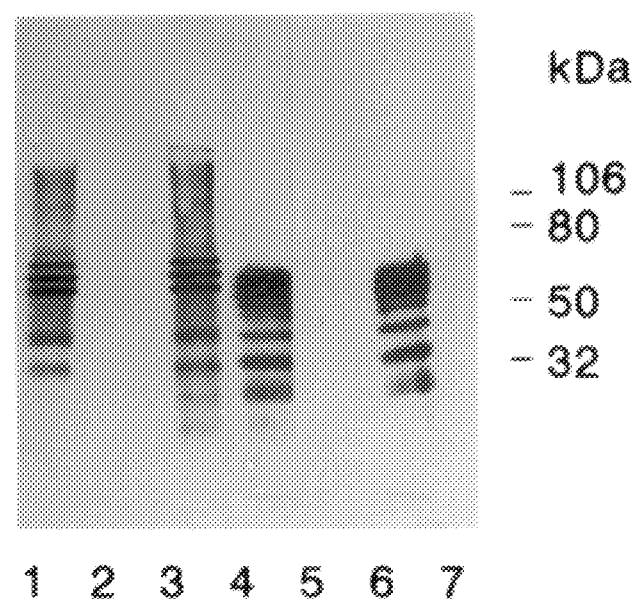
FIG. 1

Purified normal human tau and PHF-tau were applied to 10% SDS-polyacrylamide gels and run under denaturing conditions according to Laemmli (1970). After SDS-PAGE, the transfer to nitrocellulose (Hybond-C, Amersham, Brussels, Belgium) was carried out in 10 mM $NaHCO_3$, 3 mM $Na_2CO_3$, pH 9.9 for 120 min at 55V with cooling. After blotting, the nitrocellulose was equilibrated to phosphate buffered saline (PBS), and protein binding sites were blocked with blot buffer (PBS supplemented with 5% w/v skimmed dried milk and 10% v/v newborn calf serum). Blotted proteins were incubated overnight at 4° C. with AT120 as primary antibody. After 3 washings with PBS-0.05% Tween 20(v/v), horseradish peroxidase-labeled rabbit anti-mouse immunoglobulins (Dakopatts, Glostrup, Denmark) were used at a dilution of 1/3000 and were incubated for 90 min at room temperature. All antisera were diluted in blot buffer. The blots were then washed three times in PBS/Tween and developed with substrate solution (PBS, 0.05% w/v 3,3'-diaminobenzidine, 0.03% v/v $H_2O_2$) after which the reaction was stopped in $H_2O$. Results shown in FIG. 1 indicate, that the AT120 antibody recognizes all tau isoforms. By contrast, the Tau-1 antibody (Binder et al., 1985) reacts solely with normal tau, and the AT8 antibody (Mercken et al., 1992b) only with PHF-tau.

AT120, AT8 and Tau-1 mAbs were tested for phosphatase sensitivity of their epitopes in ELISA and in Western Blot on PHF-tau antigen. The reactivity of the AT120 antibody with PHF-tau was not sensitive to phosphatase treatment either in ELISA (data not shown) or on Western blots (data not shown). The reactivity of AT8 was almost completely abolished after alkaline phosphatase treatment of the PHF-tau antigen in ELISA. Dephosphorylation of PHF-tau enhanced Tau-1 immunoreactivity, as described previously (Binder et al., 1985).

Example III
Detection of tau by immunohistochemistry

Paraffin sections of formalin-fixed brain tissue from neocortex, hippocampus, cerebellum, pons, and spinal cord of several Alzheimer patients and age-matched controls were prepared, as well as sections of peripheral nerve from one control patient.

Cryostat sections from Alzheimer and age-matched control brain were also prepared. Tissues were immunostained either with the peroxidase-antiperoxidase (PAP) technique (Steinberger et al., 1970) or with the avidin-biotin complex (ABC) technique (Hsu et al., 1981) using Dakopatts (Denmark) and Amersham (UK) reagents, respectively.

Briefly, after blocking non-specific interactions with normal swine serum (Dakopatts X901) diluted 1:25 in Tris-buffered saline (TBS) containing 1% bovine serum albumin (BSA), sections were incubated overnight with the AT120 primary antibody appropriately diluted in TBS/BSA. Secondary antibody and peroxidase complex were then applied for 30 min each, with intermediate rinsing in TBS. Color was developed with 3,3'-diaminobenzidinetetrahydrochloride (Sigma). Sections were counterstained with Harris' hematoxylin, dehydrated, coverslipped, and viewed under a light microscope.

FIGS. 2A and 2B clearly indicate that AT120 produces abundant staining of NFT, dystrophic neurites in plaques, and dispersed staining of neuropil (neuropil threads).

Example IV
Detection of tau in cerebrospinal fluid samples
Cerebrospinal fluid samples CSF samples from patients were collected at the Department of Neurology of the University Hospital of Antwerp. All samples were obtained by lumbar puncture performed for routine diagnostic purposes. CSF samples were frozen and kept at $-75°$ C. in small aliquots until use.

The patients were divided into 3 different groups: 27 patients diagnosed with probable AD according to Mc Khann et al. (1984), mentally healthy control patients, who underwent lumbar puncture for radiculopathy and patients suffering from other neurological diseases (OND). The OND group included inflammatory, vascular, and other diseases, including patients with neurodegenerative diseases such as adenoleukodystrophy, frontal lobe degeneration, cerebellar atrophy, olivo-ponto-cerebellar atrophy, and amyotrophic lateral scelerosis. The age, sex and diagnosis were noted for each patient.

AT120 assay

AT120 monoclonal antibodies purified from serum-free conditioned medium by Protein G column chromatography were coated overnight at 4° C. on high-binding microtiter plates (Nunc, Gibco, Paisley, UK) in coating buffer at 3 $\mu$g/ml (10 mM Tris, 10 mM NaCl, 10 mM $NaN_3$, pH 8.5). After overcoating for 30 min with 150 $\mu$l 10%-saturated casein in PBS to reduce non-specific binding, the plates were incubated with 25 $\mu$l CSF and 75 $\mu$l conjugate mixture containing 0.2 $\mu$g/ml of biotynilated $BT_2$ and an equal amount of HT7 in 5% Tween 20, 10% saturated casein in PBS. The plates were left overnight at room temperature and after washing peroxidase conjugated streptavidine (Jackson) (1/15000) was added for 30 minutes at room temperature.

Following an additional washing, 100 $\mu$l 0.42 mM 3,5, 3', 5'-tetramethylbenzidine 0.003% $H_2O_2$ v/v in 100 mM citric acid, 100 mM disodium hydrogen phosphate, pH 4.3, were added as perocidase substrate. The reaction was stopped with 50 $\mu$l of a 2M $H_2SO_4$ solution. Absorbance was read in a Titertech Multiscan (Flow laboratories, Eflab, Oy, Finland) at 450 nm, Absorbance values obtained with AT120 from the CSF samples were compared with standard curves generated from known quantities of affinity purified normal human tau and this comparison allowed the result to be expressed as pg tau/ml.

A summary of these results are compiled in Table II, where patients ID, diagnosis, age and tau values expressed in pg/ml CSF are listed. From these results, it is obvious that levels of control patients are substantially lower (mean: 16.4 pg/ml) as compared to the group of patients suffering from various neurological diseases (OND; mean value: 26.4 pg/ml). For patients with Alzheimer's disease the mean value is clearly elevated above those of control and OND samples (mean Alzheimer patient: 50.8 pg/ml). If a cut-off level of 27 pg/ml is adopted, 8% of the control samples are positive, while for the OND group and the Alzheimer group these values are 27% and 80% respectively.

TABLE II

Tau levels as determined with the AT120 ELISA assay, grouped according to control patients, Alzheimer patients (AD) and other neurological diseases (OND) and according to age cohort, expressed in pg/ml. Mean and Std (=SD) is expressed as pg/ml per age cohort.

| Number | Diagnosis | Age | pg/ml | mean | Std |
|---|---|---|---|---|---|
| 3 | AD (early onset AD) | 35 | * 56.5 | 33.3 | 12.3 |
| 260 | A.D. | 41 | * 31.2 | | |
| 113 | A.D. | 44 | * 42.6 | | |
| 161 | A.D. (possibly Creutzfeld) | 57 | * 33.8 | | |
| 81 | A.D. | 58 | * 14.5 | | |
| 126 | A.D. | 59 | * 24.8 | | |
| 421 | A.D. | 59 | * 29.8 | | |
| 338 | A.D. | 64 | * 51.2 | 61.68 | 35.4 |
| 254 | A.D. | 66 | * 80.2 | | |
| 209 | A.D. | 67 | * 74.4 | | |
| 383 | Primary degenerative dementia | 67 | * 32.5 | | |
| 38 | A.D. | 67 | * 68.7 | | |
| 229 | A.D. | 73 | * 70.9 | | |
| 132 | A.D. | 76 | * 51.9 | | |

TABLE II-continued

Tau levels as determined with the AT120 ELISA assay, grouped according to control patients, Alzheimer patients (AD) and other neurological diseases (OND) and according to age cohort, expressed in pg/ml. Mean and Std (=SD) is expressed as pg/ml per age cohort.

| Number | Diagnosis | Age | pg/ml | mean | Std |
|---|---|---|---|---|---|
| 88 | A.D. | 76 | * 25.3 | | |
| 65 | Dementia | 77 | * 80.1 | | |
| 71 | A.D. | 78 | * 53.9 | | |
| 28 | A.D. (early onset A.D.) | 78 | * 48.7 | | |
| 11 | A.D. | 85 | * 14 | | |
| 39 | A.D. | 86 | * 150 | | |
| 386 | control | 5 | * 17.5 | 17.3 | 4.37 |
| 108 | control | 20 | * 14.3 | | |
| 402 | control | 26 | * 14 | | |
| 106 | control | 27 | * 14 | | |
| 424 | control | 28 | * 14 | | |
| 355 | control | 28 | * 20.1 | | |
| 399 | control | 29 | * 14 | | |
| 373 | control | 30 | * 17.4 | | |
| 381 | control | 31 | * 14 | | |
| 372 | control | 32 | * 19.2 | | |
| 379 | control | 32 | * 18.3 | | |
| 241 | control | 32 | * 14 | | |
| 415 | control | 32 | * 14 | | |
| 428 | control | 33 | * 16.6 | | |
| 118 | control | 34 | * 21.5 | | |
| 224 | control | 36 | * 15.7 | | |
| 24 | control | 37 | * 25.2 | | |
| 369 | control | 38 | * 23.9 | | |
| 425 | control | 39 | * 14 | | |
| 145 | control | 40 | * 31.9 | | |
| 61 | control | 40 | * 17.3 | | |
| 377 | control | 40 | * 14 | | |
| 366 | control | 41 | * 17.7 | | |
| 401 | control | 41 | * 20.1 | | |
| 400 | control | 42 | * 14 | | |
| 417 | control | 42 | * 14 | | |
| 354 | control | 43 | * 16.8 | | |
| 34 | control | 43 | * 25.8 | | |
| 217 | control | 43 | * 14 | | |
| 364 | control | 44 | * 14 | | |
| 134 | control | 45 | * 16.7 | | |
| 367 | control | 45 | * 14 | | |
| 427 | control | 45 | * 14 | | |
| 394 | control | 48 | * 14 | | |
| 361 | control | 48 | * 14 | | |
| 237 | control | 50 | * 17.2 | | |
| 396 | control | 52 | * 16.4 | | |
| 100 | control | 54 | * 23.9 | | |
| 411 | control | 54 | * 14 | | |
| 371 | control | 55 | * 18.4 | | |
| 423 | control | 56 | * 14.9 | | |
| 99 | control | 56 | * 27.9 | | |
| 192 | control | 60 | * 19.9 | 24.83 | 15.17 |
| 387 | control | 61 | * 14 | | |
| 389 | control | 65 | * 19.5 | | |
| 426 | control | 66 | * 15.4 | | |
| 141 | control | 67 | * 14 | | |
| 368 | control | 67 | * 15.4 | | |
| 60 | control | 77 | * 43.5 | | |
| 348 | control | 80 | * 56.9 | | |
| 419 | Hydrocephalus | 0 | * 150 | 29.35 | 26.78 |
| 413 | Adenoleukodystrofy | 13 | * 23.1 | | |
| 376 | Paresthesia | 14 | * 21.1 | | |
| 239 | Epilepsy, encephalitis | 16 | * 29.8 | | |
| 7 | SSPE | 17 | * 48.1 | | |
| 139 | Cerebellitis (Mycoplasma p.) | 18 | * 19.7 | | |
| 180 | *Herpes encephalitis* | 19 | * 14.1 | | |
| 206 | CBS | 20 | * 15.9 | | |
| 140 | TC ? | 21 | * 14.2 | | |
| 228 | Ishernic cerebral infarct | 22 | * 150 | | |
| 197 | Kawasaki | 24 | * 27.8 | | |
| 133 | MS | 24 | * 37.1 | | |
| 212 | Alcohol PNP | 25 | * 14 | | |
| 66 | MS ? | 25 | * 14 | | |
| 143 | Myopathy | 25 | * 18.3 | | |
| 82 | MS | 26 | * 20.2 | | |
| 258 | Guillian-Barré | 26 | * 14.4 | | |
| 105 | MS | 26 | * 18.4 | | |
| 169 | Dementia ? | 27 | * 37.5 | | |
| 351 | Viral meningitis | 28 | * 17.3 | | |
| 213 | MS | 28 | * 15.7 | | |
| 253 | Encephalitis viral ? | 28 | * 38.1 | | |
| 236 | Migraine | 29 | * 17.3 | | |
| 405 | Guillian-Barré | 29 | * 47.6 | | |
| 72 | MS | 29 | * 14 | | |
| 234 | MS | 29 | * 19.9 | | |
| 128 | GBS | 29 | * 14 | | |
| 138 | PNP | 32 | * 17.6 | | |
| 218 | Empty sella | 35 | * 14 | | |
| 135 | MS | 35 | * 16.3 | | |
| 346 | Neuritis optico | 35 | * 14 | | |
| 117 | Trigeminus neurology | 36 | * 14 | | |
| 350 | MS | 37 | * 14 | | |
| 384 | Guillian-Barré | 37 | * 14 | | |
| 123 | CVA | 38 | * 14 | | |
| 56 | TIA (transient ischemic attack) | 39 | * 14.9 | | |
| 172 | CVA ? psych. | 40 | * 21.7 | | |
| 189 | Hemicranial headache | 41 | * 15.9 | | |
| 119 | Amyloidosis | 42 | * 15.3 | | |
| 69 | Meningitis | 42 | * 26.5 | | |
| 231 | Contuno alcohol | 42 | * 15.5 | | |
| 130 | External oftalmoplegia | 43 | * 53.6 | | |
| 357 | CVA | 44 | * 16.6 | | |
| 391 | MS | 44 | * 14 | | |
| 62 | MS ?? | 44 | 21.2 | | |
| 124 | Syphilis | 45 | * 20.4 | | |
| 89 | PNP | 45 | * 27.1 | | |
| 122 | *Cauda equina* syndroom etiol. | 46 | * 14 | | |
| 249 | MS | 47 | * 14 | | |
| 112 | MS ? | 48 | * 14.9 | | |
| 363 | Encephalitis | 48 | * 35.9 | | |
| 125 | MS | 48 | * 24.9 | | |
| 205 | GBS | 49 | | | |
| 388 | MS | 50 | * 14 | | |
| 418 | Tetanos | 50 | * 14 | | |
| 207 | GBS ? | 50 | * 70.3 | | |
| 114 | Cerebellar atrofy | 51 | * 51.5 | | |
| 121 | Syphilis | 51 | * 28.1 | | |
| 35 | MS + PNP (diabetic) | 51 | * 17.3 | | |
| 215 | OLM | 52 | * 14 | | |
| 101 | Brain infarct | 53 | * 52.8 | | |
| 255 | PNP + (MS ?), diabetic | 53 | * 18.4 | | |
| 173 | Lyme disease | 54 | * 17.5 | | |
| 360 | (Borrelia) (MS-like) | 54 | * 34.7 | | |
| 374 | ALS | 54 | * 65.3 | | |
| 179 | Lyme disease | 54 | * 16.4 | | |
| 50 | Epilipsy-alcoholism | 55 | * 21.5 | | |
| 184 | Epilepsia | 55 | * 16.7 | | |
| 210 | MS | 56 | * 16.2 | | |
| 58 | CVA | 57 | * 25.3 | | |
| 137 | Pick ? | 57 | * 77.4 | | |
| 131 | Meningial bleeding | 57 | * 66.7 | | |
| 398 | Meningoencephalis | 58 | * 117.8 | | |
| 349 | Meningoencephalis | 58 | * 35.6 | | |
| 244 | *Facialis parese* | 58 | * 18.5 | | |
| 219 | Pseudobullair syndrome | 58 | * 39.6 | | |
| 64 | MS | 58 | * 40.7 | | |
| 36 | TIA | 59 | * 14 | | |
| 240 | Guillian-Barré | 68? | * 14 | 25.06 | 15.69 |
| 70 | *N. ulnaris*/Parkinson (?) | 60 | * 23.8 | | |
| 166 | tbc | 60 | * 14 | | |
| 85 | Aneurism | 60 | * 18.3 | | |
| 204 | Bipyramidal idiopathy | 60 | * 16.8 | | |
| 167 | Cerebellar atrophy | 61 | * 14 | | |
| 157 | Bulbar paralysis | 62 | * 17.4 | | |
| 30 | Steele Richardson | 62 | * 19.2 | | |
| 153 | Lymfora CSZ | 62 | * 22.2 | | |

TABLE II-continued

Tau levels as determined with the AT120 ELISA assay, grouped according to control patients, Alzheimer patients (AD) and other neurological diseases (OND) and according to age cohort, expressed in pg/ml. Mean and Std (=SD) is expressed as pg/ml per age cohort.

| Number | Diagnosis | Age | pg/ml | mean | Std |
|---|---|---|---|---|---|
| 414 | Subacute polyneuropathy | 62 | * 14 | | |
| 37 | OPCA | 63 | * 26.7 | | |
| 109 | Pick; ALS | 63 | * 40.5 | | |
| 277 | COLD | 64 | * 14 | | |
| 195 | E, dialysis | 64 | * 14 | | |
| 148 | MS | 65 | * 15.4 | | |
| 375 | Polyneuropathy, Charot-Marie-Tooth | 65 | * 15.5 | | |
| 182 | ALS | 65 | * 14 | | |
| 230 | Parkinson | 66 | * 21.1 | | |
| 409 | Multiple vascular (pons.) | 66 | | | |
| 170 | Temp. E | 66 | * 24.2 | | |
| 186 | ALS | 66 | * 21.2 | | |
| 59 | Menigeal aneurysma | 67 | * 28.4 | | |
| 233 | Korsakow-like post trauma | 67 | * 29.6 | | |
| 120 | ALS | 67 | * 25.7 | | |
| 550 | PNP, CVA, diabetes | 67 | * 64.2 | | |
| 110 | Diabetes | 67 | * 14 | | |
| 259 | Polyvascular syndrome + demyelinisation | 68 | | | |
| 248 | (?) | 68 | * 14 | | |
| 235 | CVA | 68 | * 77.9 | | |
| 362 | Guillain-Barré | 68 | * 14 | | |
| 208 | PNP-zona | 68 | * 28.8 | | |
| 115 | Subacute combined degeneration | 68 | * 14 | | |
| 98 | TIA | 68 | * 34.9 | | |
| 193 | GBS | 68 | * 44.1 | | |
| 222 | Guillain-Barré | 69 | * 14.1 | | |
| 102 | PNP | 70 | * 14 | | |
| 242 | Bipyramidal syndrome PNP | 72 | * 20.8 | | |
| 251 | Trauma cerebri commoti | 77 | * 14 | | |
| 422 | Infarct | 78 | * 20.7 | | |
| 42 | Multi-infarct dementia | 78 | * 38.9 | | |
| 93 | Diabetes, PNP, radiculopathy | 85 | * 61.9 | | |
| 53 | Mixed dementia, Parkinson | 85 | * 59.3 | | |

Abbreviations:
SSPE: Subacute sclerosing panencephalitis,
GBS: Guillain-Barré syndrome,
TC: Meningeal tuberculosis,
MS: Multiple sclerosis,
PNP: Polyneuropathy,
CVA: cerebrovascular amyloidosis,
ALS: Amyotrophic lateral sclerosis,
TIA: Transient ischemic attack,
OPCA: Olivo-ponto cerebellar atrophy,
COLD: Chronic obstructive lung disease.

Example V
Definition of the AT120 epitope

Since AT120 reacts equally well with all isoforms of tau (Goedert et al., 1989), the smallest recombinant tau form was used for deletion mapping. To this, two sites were used for deletion construction, the SacII site at position 155 of the human tau 34 sequence and the SmaI site position 220 (Goedert et al., 1989). A mTNF-fusion vector pmTNF (MPH) (Innogenetics, Ghent, Belgium), in which the smallest tau open reading frame was fused to 25 amino acids of mouse tumor necrosis factor, was cut with ApaI-SacII, blunted with $T_4$ DNA polymerase and ligated. After cutting the ligated material with Sac II and Apa I to reduce non-mutant background, the mixture was transformed into MC1061 pc I587 (Casadaban & Cohen, (1980)). Each selected clone was further characterized by restriction digestion and by its reactivity with anti-tau antibodies.

Figure 4:
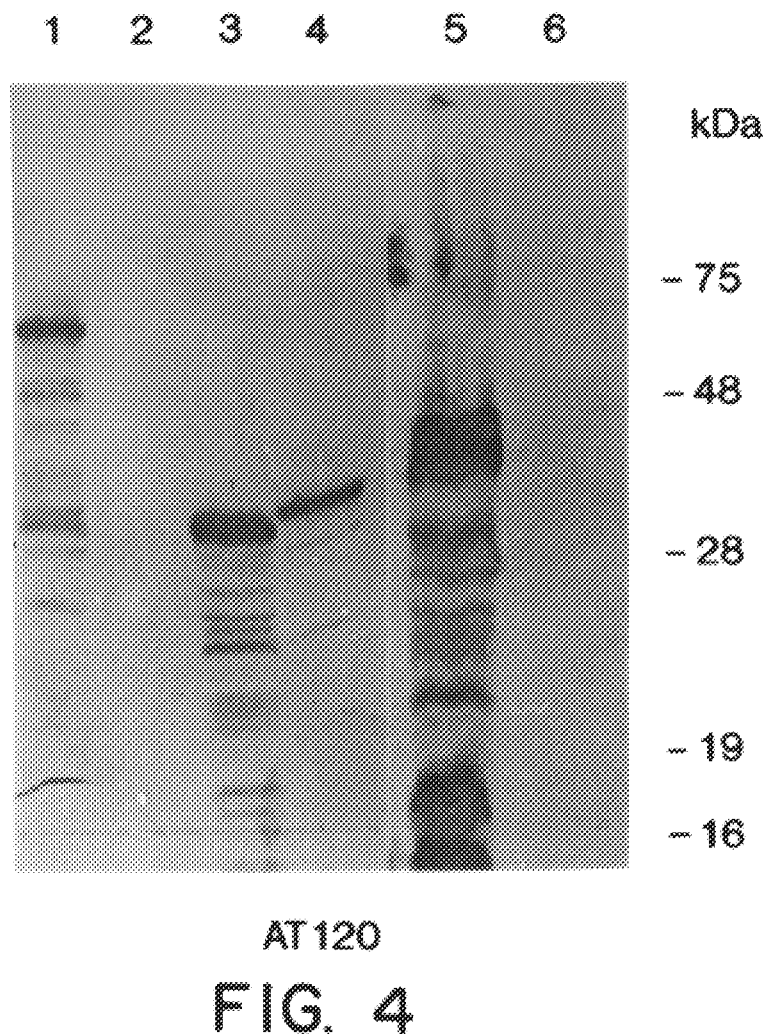

The same mouse TNF fusion tau vector was used to insert a frame shift mutation in the XmaI restriction site. The vector was cut with SmaI, blunted with $T_4$ DNA polymerase and the ligated mixture was retreated with SmaI before transformation in order to reduce non-mutant background. The reactivity pattern of each of the mutants was checked with AT120 monoclonal antibodies by means of Western Blotting. This allowed to localize the epitope of AT120 in a first approximation to the region of 65 amino acids spanning amino acid 155–221 which is represented in SEQ ID NO 1 (FIG. 4). However, since in this region also two other antibodies, BT2 (Mercken et al, 1992a) and HT7 (Mercken, Ph.d. Thesis) show reactivity it was mandatory to prove that no competition binding was observed between the latter monoclonal antibodies and AT120.

Therefore, a competition ELISA with each of these antibodies was performed. To this, affinity purified rabbit anti-human tau polyclonal antibodies were coated overnight at 4° C. in coating buffer (10 mM Tris pH 8.6, 10mM NaCl, 10mM $NaN_3$), and after blocking with 0,1% caseine in PBS, 100 μl/well of pure PHF-tau was added for 1 h at 37° C. After washing, 50 μl of either AT8, BT2 or AT120 unlabeled monoclonal antibody was added at a concentration of 10μg/ml and incubation was continued for 30 min at 37° C. Next, 50 μl of biotinylated monoclonal antibody was added. Each of these biotinylated antibodies was used in a preset concentration, which in a tau Sandwich ELISA (as described in Example II) gave 50% of the maximal OD value. After a subsequent incubation of 1 h at 37° C., the plates were further treated as described in Example II.

TABLE III

Competition ELISA using monoclonal antibodies AT8, AT120 and BT2.

| | Unlabeled competitor Absorbance | | |
|---|---|---|---|
| BIOTINYLATED | AT8 | AT120 | BT2 |
| AT8 | 0.001 | 0.372 | N.D. |
| AT120 | 0.476 | 0.001 | N.D. |
| BT2 | N.D. | 0.543 | 0.054 |

N.D. refers to not determined absorbances

The results, shown in Table III clearly indicate that the epitope recognized by the monoclonal antibody AT120 is different from the epitopes recognized by the monoclonal antibodies BT2 and AT8. Consequently, solid phase immobilized synthetic nonapeptides, the sequence of which was derived from the epitope of the invention as depicted in SEQ ID NO 1, were incubated with each of these monoclonal antibodies. The complexes were visualised as in Example I, section 3. On the basis of their respective reactivity patterns it was confirmed that the epitope recognized by AT120 is different from that of each of the other monclonal antibodies (Table IV and FIG. 5)

TABLE IV

Reactivity of monoclonal antibodies BT2, HT7 and AT120 with solid phase bound nonapeptides.
The nonapeptides are designated in the one-letter amino acid code.

| | Detecting Monoclonal antibody Absorbance | | |
|---|---|---|---|
| Nonapeptides | HT7 | BT2 | AT120 |
| GAAPPGQKG (SEQ ID NO 5) | 3.00 | 0.168 | 0.089 |
| GDRSGYSSP (SEQ ID NO 6) | 0.493 | 3.00 | 0.553 |

In addition to these experiments, the AT120 epitope was also confirmed by peptide mapping. Hereto, a total of 20 μg of mTNF-MPHtau1 (see FIG. 6) was lyophilized and redissolved in 56 μl of 100 mM Tris HCl containing 10% acetonitrile. To this was added 14 μl of endoprotease Asp N (0.04 ug/ml) and the mixture was incubated for 8 hours at 37° C. Following cleavage, the mixture was divided equally over 5 sample wells and subjected to SDS-polyacrylamide gel electrophoresis. Following electrophoresis, the peptides in the gel were blotted onto a PVDF membrane. A strip of the PVDF membrane corresponding to one lane on the gel was removed. Free binding sites on the membrane were blocked by incubation with 0.5% casein in PBS, and the strip was incubated with the monoclonal antibody AT120 to determine if protein fragments were present which were capable of being recognized. The presence of bound antibody was detected using an alkaline phosphatase-labeled rabbit anti-mouse conjugate followed by incubation with 5-bromo-4-chloro-3-indolyl phosphate and nitro blue tetrazolium. The remainder of the PVDF membrane was stained with Amido Black, which revealed the presence of 5 bands, all with a molecular size smaller than that of the original protein. One of these bands was visible on the portion of the blot which was incubated with AT120. The band which was specifically recognized by AT120 corresponded to the largest of the Amido Black-stained bands with an apparent molecular size of approximately 6 kDa. This band was excised from the Amido Black-stained blot and subjected to amino terminal sequence analysis (Edman degradation). The analysis revealed that the band recognized by AT120 began with Asp193 in the amino acid sequence of tau, close to the C-terminus of the tau sequence contained within the mTNF-MPHtau1 recombinant protein.

It thus appeared probable, that additional amino acid sequences located downstream with respect to Arg221 might be required for binding of the monoclonal antibody AT120. In order to test this hypothesis in an attempt to further delineate the boundaries of the epitope, peptide (tau5B) was synthesized:

| PEPTIDE SEQUENCE | REACTION WITH AT120 |
|---|---|
| GGSRSRTPSLPT (SEQ ID NO 8) | – |
| GSRSRTPSLPTP (SEQ ID NO 9) | – |
| SRSRTPSLPTPP (SEQ ID NO 10) | – |
| RSRTPSLPTPPT (SEQ ID NO 11) | – |
| SRTPSLPTPPTR (SEQ ID NO 12) | – |
| RTPSLPTPPTRE (SEQ ID NO 13) | – |
| TPSLPTPPTREP (SEQ ID NO 14) | – |
| PSLPTPPTREPK (SEQ ID NO 15) | +++ |
| SLPTPPTREPKK (SEQ ID NO 16) | +++ |
| LPTPPTREPKKV (SEQ ID NO 17) | +++ |
| PTPPTREPKKVA (SEQ ID NO 18) | +++ |
| TPPTREPKKVAV (SEQ ID NO 19) | +++ |
| PPTREPKKVAVV (SEQ ID NO 20) | +++ |
| PTREPKKVAVVR (SEQ ID NO 21) | – |
| TREPKKVAVVRT (SEQ ID NO 22) | – |

From this experiment, it is evident that the epitope recognized by AT120 is a linear sequence comprised of amino acids Pro218 to Lys224 as specified in SEQ ID NO 4.

REFERENCES

Barton A, Harrison P, Najlerahim A, Heffernan J, McDonald B, Robison J, Davies D, Harrison W, Mitra P, Hardy J, Pearson R, (1990) Increased tau messenger RNA in Alzheimer's disease hippocampus. Am J Pathol, 137:497–502.

Baudier J, Cole R (1987) Phosphorylation of Tau proteins to a state like that in Alzheimer's brain is catalyzed by a calcium/calmodulin-dependent kinase and modulated by phospholipids. J Biol Chem 262:17577–17583.

Biernat J, Mandelkow M, Schoter C, Lichtenberg-Kraag B, Steiner B, Berling B, Meyer H, Mercken M, Vandermeeren M, Mandelkow E, The switch of tau protein to an Alzheimer-like state includes the phosphorylation of two

```
                 208    210              215
tau5B    Bio—Gly Gly Ser Arg Ser Arg Thr Pro Ser Leu Pro Thr
         220             225              230 231
Pro Pro Thr Arg Glu Pro Lys Lys Val Arg Val Val Arg Thr (SEQ ID NO 7)
```

Since it cannot be excluded that the second glycine residue of the spacer sequence is functionally equivalent to Gly207, the position of the epitope bound by AT120 must lie between Gly207 and Thr231.

In order to localize the epitope within the sequence of peptide tau5B even more precisely, overlapping 12-mers spanning the tau5B sequence were synthesized in quadruplicate as defined spots on Whatman 1MM paper. The paper was first derivatized with two residues of β-alanine to provide the paper with a handle on which peptide synthesis could take place. The first of these β-alanine residues was coupled as a symmetric anhydride in the presence of 1 equivalent of dimethylaminopyridine. The second β-alanine residue was coupled following in situ activation using 2-(1H-benzotriazol-1-yl)-1,1,3 ,3-tetramethyluronium tetrafluoroborate in the presence of 1-hydroxybenzotriazole. The coupling of all additional amino acids was performed using the same chemistry (Knorr et al., 1989). The peptides synthesized and their recognition by AT120 were as follows:

serine-proline motifs upstream of the microtubule binding region. EMBO J, 1992, 11:1593–1597.

Binder L, Frankfurter A, Rebhun L (1985) The distrubution of Tau in the mammalian central nervous system. J Cell Biol 101:1371–1378.

Bobrow M, Harris T, Shaughnessy K, Litt G (1989) Catalyzed reporter deposition, a novel method of signal amplification. Application to immunoassays. J Immunol Meth 125:279–285.

Bré M, Karsenti E (1990) Effects of brain microtubule-associated proteins on microtubule dynamics and the nucleating activity of centrosomes. Cell Motil Cytoskeleton 15:88–98.

Brion J, Couck A, Passareiro E, Flament-Durand J (1985) Neurofibrillary tangles of Alzheimer's disease: an immunohistochemistry study. J Submicrosc Cytol 17:89–96.

Casacdaban M, Cohen S (1980), Analysis of gene control signals by DNA fusion and cloning in *Eschericia coli*. J Mol Biol, 138:179–207.

De Bont H, Van Boom J, Liskamp R (1990) Automatic synthesis of phosphopeptides by phosphorylation on the solid phase. Tetrahedron Lett 31:2497–2500.

Delacourte A, Vermersch P (1992) Abnormally phosphorylated tau proteins in Alzheimer's disease: a diagnostic test ? Breakthroughs in Alzheimer's disease, 5–6March, London, p. 1–4.

Delacourte A, Flament S, Dibe E, Hublau P, Sablonniere B, Hemon B, Sherrer V, Defossez A (1990) Pathological proteins Tau64 and 69 are specifically expressed in the somatodendritic domain of the degenerating cortical neurons during Alzheimer's disease. Acta Neuropathol 80:111–117.

Flament S, Delacourte A, Hemon B, Defossez A (1989) Characterization of two pathological Tau protein variants in Alzheimer brain cortices. J Neurol Sci 92:133–141.

Flament S, Delacourte A (1990) Tau Marker? Nature 346:6279.

Flament S, Delacourte A, Mann D (1990) Phosphorylation of tau proteins: a major event during the process of neurofibrillary degeneration. A comparitive study between Alzheimer's disease and Down's syndrome. Brain Res 516:15–19.

Ghanbari H, Kozuk T, Miller B, Riesing S (1990) A sandwich enzyme immunoassay for detecting and measuring Alzheimer's disease-associated proteins in human brain tissue. J Clin Laboratory Anal 4:189–192.

Goedert M, Wishik C, Crowther R, Walker J, Klug A, Cloning and sequencing of the cDNA encoding a core protein of the paired helical filament of Alzheimer disease: identification as the microtubuli-associated protein tau. Proc Natl Acad Sci USA, 1988, 85, 4051–4055

Goedert M, Spillantini M, Jakes R, Rutherford D, Crowther R (1989) Multiple isoforms of human microtubule-associated protein tau: sequences and localization in neurofibrillary tangles of Alzheimer's disease. Neuron 3:519–526.

Goedert M, Spillantini M, Jakes R (1991) Localization of the Alz-50 epitope in recombinant human microtubule-associated protein tau. Neurosci Lett. 126:149–154.

Goedert M, Cohen E, Jakes R, Cohen P (1992) p42Map kinase phosphorylation sites in microtubule-associated protein tau one dephosphorylated by protein phosphatase 2A1 implications for Alzheimer's disease. FEBS Lett. 312:95–99.

Greenberg S, Davies P (1990) A preparation of Alzheimer paired helical filaments that displays distinct tau proteins by polyacrylamide gel electrophoresis. Proc Natl Acad Sci USA 87:5827–5831.

Harrington C, Edwards P, Wischik C (1990) Competitive ELISA for the measurement of tau protein in Alzheimer's disease. J Immunol Methods 134:261–271.

Himmler A (1989) Structure of the bovine Tau gene: alternatively spliced transcripts generate a protein family. Mol Cell Biol 9:1389–1396.

Hsu S, Raine L, Fanger H (1981) Use of avidin-biotin-peroxidase complex (ABC) in immunoperoxidase techniques: a comparison between ABC and unlabeled antibody (PAP) procedures. J Histochem Cytochem 29:577–580.

Iqbal K, Zaidi T, Thompson C, Merz P, Wisniewski H (1984) Alzheimer paired helical filaments: bulk isolation, solubility, and protein composition. Acta Neuropathol 62:167–177.

Ishiguro K, Ihara Y, Uchida T, Imahori K (1988) A novel tubulin-dependent protein kinase forming a paired helical filament epitope on tau. J Biochem 104:319–321.

Khatoon S, Grundke-Iqbal I, Iqbal K (1992) Brain levels of microtublule-associated protein tau are elevated in Alzheimer's disease: a radioimmuno-slot-blot assay for nanograms of the protein. J Neurochem 59:750–753.

Knorr R, Trzeciak A, Bannwarth W, Gillessen D (1989) New coupling reagents in peptide chemistry. Tetrahedron Letters 30:1927–1930.

Kosik K, Orecchio L, Binder L, Trojanowski J, Lee V, Lee G (1988) Epitopes that span the Tau molecule are shared with paired helical filaments. Neuron 1:817–825.

Kosik K, Candall J, Mufson E, Neve R (1989) Tau in situ hybridization in normal and Alzheimer brain: A predominant localization in the neuronal somatodendritic compartment. Ann Neurol 26:352–361.

Ksiezak-Reding H, Dickson D, Davies P, Yen S (1987) Recognition of tau epitopes by anti-neurofilament antibodies that bind to Alzheimer neurofibrillary tangles. Proc Natl Acad Sci USA 84:3410–3414.

Ksiezak-Reding H, Chien C, Lee V, Yen S (1990) Mapping of the Alz50 epitopes in microtubule-associated proteins tau. J Neurosci Res 25:412–419.

Köhler G, Milstein (1975) Continuous cultures of fused cells secreting antibody of predefined specificity. Nature 256:495–497.

Laemmli U (1970) Cleavage of structural proteins during the assembly of the head of bacteriophage T4. Nature 227:680–685.

Lee V, Balin B, Otvos L, Trojanowski J (1991) A68: a major subunit of paired helical filaments and derivatized forms of normal tau. Science 251:675–678.

Lewis S, Wang D, Cowan N (1988) Microtubule-associated protein MAP2 shares a microtubule binding motif with Tau protein. Science 242:936–939.

Lindwall G, Cole R (1984) The purification of tau proteins and the occurrence of two phosphorylation states of tau in brain. J Biol Chem 259:12241–12245.

Mehta P, Thal L, Wisniewski H, Grundke-Iqbal I, Iqbal K (1985) Paired helical filament antigen in CSF. The Lancet 2:35.

Mercken M, Vandermeeren M, Lubke U, Six J, Boons J, Vanmechelen E, Van de Voorde A, Gheuens J (1992a) Affinity purification of human tau proteins and the construction of a sensitive sandwich enzyme-linked immunosorbent assay for human tau detection. J Neurochem 58:548–553.

Mercken M, Vandermeeren M, Lubke U, Six J, Boons J, Van de Voorde A, Martin J J, Gheuens J (1992b) Monoclonal antibodies with selective specificity for Alzheimer Tau are directed against phosphatase-sensitive epitopes. Acta Neuropathol 84:265–272.

Nukina N, Kosik K S, Selkoe D (1987) Recognition of Alzheimer paired helical filaments by monoclonal neurofilament antibodies is due to crossreaction with tau protein. Proc Natl Acad Sci USA 84:3415–3419.

Nukina N, Kosik K, Selkoe D (1988) The monoclonal antibody, Alz 50, recognizes tau proteins in Alzheimer's disease brain. Neurosci Lett 87:240–246.

Papasozomenos S, Binder L (1987) Phosphorylation determines two distinct species of tau in the central nervous system. Cell Motility Cytoskeleton 8:210–226.

Sternberger L A, Hardy P H, Cuculis P H, Meyer H G (1970) The labeled antibody enzyme method of immunohistochemistry: preparation and properties of soluble antigen-antibody complex (horseradish peroxidase-antihorseradish peroxidase) and its use in identification of spirochetes. J Histochem Cytochem 18:315–333.

Steiner B, Mandelkow E, Biernat J, Gustke N, Meyer H, Schmidt B, Mieskes G, Soling H, Drechsel D, Kirschner M, Goedert M, Mandelkow E (1990) Phophorylation of microtubule-associated protein tau: identification of the site for $Ca^{2+}$-calmodulin dependent kinase and relationship with tau phosphorylation in Alzheimer tangles. The EMBO J 9:3539–3544.

Towbin H, Staehelin T, Gordon J (1979) Electrophoretic transfer of proteins form polyacrylamide gels to nitrocellulose sheets: procedure and some applications. Proc Natl Acad Sci USA 76:4350–4354.

Vallee R (1982) A taxol-dependent procedure for the isolation of microtubules and microtubule-associated proteins (MAPs). J Cell Biol 92:435–442.

Weingarten M, Lockwood A, Hwo S, Kirschner M (1975) A protein factor essential for microtubule assembly. Proc Nat Acad Sci USA 72:1858–1862.

Wischik C, Novak M, Edwards P, Klug A, Tichelaar W, Crowther R (1988) Structural characterization of the core of the paired helical filament of Alzheimer disease. Proc Natl Acad Sci USA 85:4884–4888.

Wolozin B, Davies P (1987) Alzheimer-related neuronal protein A68: specificity and distribution. Ann Neurol 22:521–526.

We claim:

1. A method for detecting a disease involving alterations in tau protein by the quantification of total phosphorylated and unphosphorylated tau protein comprising:
  (a) contacting a sample from a patient suspected of suffering from Alzheimer's disease or any other disease involving alterations in tau protein with a monoclonal antibody produced by the hybridoma AT120 under conditions that form a tau-antibody complex, wherein the sample is selected from the group consisting of cerebrospinal fluid, serum, a neurofibrillary tangle preparation, and a detergent extracted brain homogenate;
  (b) quantifying the amount of total tau by detecting the amount of total phosphorylated and unphosphorylated tau protein in the tau-antibody complex, wherein an increase in the amount of total tau when compared to a normal healthy control is indicative of disease.

2. A method for detecting a disease involving alterations in tau protein by the quantification of total phosphorylated and unphosphorylated tau protein comprising:
  (a) contacting a sample isolated from a patient suspected of suffering from a neurological disorder involving alterations in tau protein with a monoclonal antibody produced by the hybridoma AT120 under conditions that form a tau-antibody complex;
  (b) quantifying the amount of total tau by detecting the amount of total phosphorylated and unphosphorylated tau protein in the tau-antibody complex, wherein an increase in the amount of total tau when compared to a normal healthy control is indicative of disease.

3. The method of claim 2 wherein the sample to be tested is an unconcentrated cerebrospinal fluid (CSF) sample.

4. The method of claim 2 wherein the disorder is Alzheimer's disease.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
( A ) LENGTH: 67
( B ) TYPE: Amino Acid
( C ) STRANDEDNESS: Unknown
( D ) TOPOLOGY: linear ( x i ) SEQUENCE DESCRIPTION: SEQ ID NO: 1:

```
Arg Gly Ala Ala Pro Pro Gly Gln Lys Gly Gln Ala Asn
 1               5                   10
Ala Thr Arg Ile Pro Ala Lys Thr Pro Pro Ala Pro Lys
    15                  20                      25
Thr Pro Pro Ser Ser Gly Glu Pro Pro Lys Ser Gly Asp
            30                  35
Arg Ser Gly Tyr Ser Ser Pro Gly Ser Pro Gly Thr Pro
40                      45                  50
Gly Ser Arg Ser Arg Thr Pro Ser Leu Pro Thr Pro Pro
        55                  60                  65
Thr Arg
```

( 2 ) INFORMATION FOR SEQ ID NO: 2:

( i ) SEQUENCE CHARACTERISTICS:
( A ) LENGTH: 33
( B ) TYPE: Amino Acid
( C ) STRANDEDNESS: Unknown
( D ) TOPOLOGY: Unknown ( x i ) SEQUENCE DESCRIPTION: SEQ ID NO: 2:

```
Ser Pro Gly Ser Pro Gly Thr Pro Gly Ser Arg Ser Arg
 1               5                   10
Thr Pro Ser Leu Pro Thr Pro Pro Thr Arg Glu Pro Lys
    15                  20                      25
Lys Val Ala Val Val Arg Thr
            30
```

( 2 ) INFORMATION FOR SEQ ID NO: 3:

( i ) SEQUENCE CHARACTERISTICS:
( A ) LENGTH: 13
( B ) TYPE: Amino Acid
( C ) STRANDEDNESS: Unknown
( D ) TOPOLOGY: Unknown ( x i ) SEQUENCE DESCRIPTION: SEQ ID NO: 3:

```
Gly Ser Arg Ser Arg Thr Pro Ser Leu Pro Thr Pro Pro
 1               5                   10
```

(2) INFORMATION FOR SEQ ID NO: 4:

(i) SEQUENCE CHARACTERISTICS:
        (A) LENGTH: 7
        (B) TYPE: Amino Acid
        (C) STRANDEDNESS: Unknown
        (D) TOPOLOGY: Unknown (xi) SEQUENCE DESCRIPTION: SEQ ID NO: 4:

Pro Pro Thr Arg Glu Pro Lys
 1                   5

(2) INFORMATION FOR SEQ ID NO: 5:

(i) SEQUENCE CHARACTERISTICS:
        (A) LENGTH: 9
        (B) TYPE: Amino Acid
        (C) STRANDEDNESS: Unknown
        (D) TOPOLOGY: Unknown (xi) SEQUENCE DESCRIPTION: SEQ ID NO: 5:

Gly Ala Ala Pro Pro Gly Gln Lys Gly
 1                   5

(2) INFORMATION FOR SEQ ID NO: 6:

(i) SEQUENCE CHARACTERISTICS:
        (A) LENGTH: 9
        (B) TYPE: Amino Acid
        (C) STRANDEDNESS: Unknown
        (D) TOPOLOGY: Unknown (xi) SEQUENCE DESCRIPTION: SEQ ID NO: 6:

Gly Asp Arg Ser Gly Tyr Ser Ser Pro
 1                   5

(2) INFORMATION FOR SEQ ID NO: 7:

(i) SEQUENCE CHARACTERISTICS:
        (A) LENGTH: 26
        (B) TYPE: Amino Acid
        (C) STRANDEDNESS: Unknown
        (D) TOPOLOGY: Unknown (xi) SEQUENCE DESCRIPTION: SEQ ID NO: 7:

Gly Gly Ser Arg Ser Arg Thr Pro Ser Leu Pro Thr Pro
 1                   5                        10
Pro Thr Arg Glu Pro Lys Lys Val Arg Val Val Arg Thr
         15                  20                 25

(2) INFORMATION FOR SEQ ID NO: 8:

(i) SEQUENCE CHARACTERISTICS:
        (A) LENGTH: 12
        (B) TYPE: Amino Acid
        (C) STRANDEDNESS: Unknown
        (D) TOPOLOGY: Unknown (xi) SEQUENCE DESCRIPTION: SEQ ID NO: 8:

Gly Gly Ser Arg Ser Arg Thr Pro Ser Leu Pro Thr
 1                   5                        10

(2) INFORMATION FOR SEQ ID NO: 9:

(i) SEQUENCE CHARACTERISTICS:
        (A) LENGTH: 12
        (B) TYPE: Amino Acid
        (C) STRANDEDNESS: Unknown ( D ) TOPOLOGY: Unknown ( x i ) SEQUENCE DESCRIPTION: SEQ ID NO: 9:

Gly Ser Arg Ser Arg Thr Pro Ser Leu Pro Thr Pro
1               5                   10

( 2 ) INFORMATION FOR SEQ ID NO: 10:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 10:

Ser Arg Ser Arg Thr Pro Ser Leu Pro Thr Pro Pro
1               5                   10

( 2 ) INFORMATION FOR SEQ ID NO: 11:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 11:

Arg Ser Arg Thr Pro Ser Leu Pro Thr Pro Pro Thr
1               5                   10

( 2 ) INFORMATION FOR SEQ ID NO: 12:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 12:

Ser Arg Thr Pro Ser Leu Pro Thr Pro Pro Thr Arg
1               5                   10

( 2 ) INFORMATION FOR SEQ ID NO:13:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 13:

Arg Thr Pro Ser Leu Pro Thr Pro Pro Thr Arg Glu
1               5                   10

( 2 ) INFORMATION FOR SEQ ID NO: 14:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 14:

Thr Pro Ser Leu Pro Thr Pro Pro Thr Arg Glu Pro
1               5                   10

( 2 ) INFORMATION FOR SEQ ID NO: 15:

( i ) SEQUENCE CHARACTERISTICS:
  ( A ) LENGTH: 12
  ( B ) TYPE: Amino Acid
  ( C ) STRANDEDNESS: Unknown
  ( D ) TOPOLOGY: Unknown ( x i ) SEQUENCE DESCRIPTION: SEQ ID NO: 15:

Pro  Ser  Leu  Pro  Thr  Pro  Pro  Thr  Arg  Glu  Pro  Lys
 1              5                          10

( 2 ) INFORMATION FOR SEQ ID NO: 16:

( i ) SEQUENCE CHARACTERISTICS:
    ( A ) LENGTH: 12
    ( B ) TYPE: Amino Acid
    ( C ) STRANDEDNESS: Unknown
    ( D ) TOPOLOGY: Unknown ( x i ) SEQUENCE DESCRIPTION: SEQ ID NO: 16:

Ser  Leu  Pro  Thr  Pro  Pro  Thr  Arg  Glu  Pro  Lys  Lys
 1              5                          10

( 2 ) INFORMATION FOR SEQ ID NO: 17:

( i ) SEQUENCE CHARACTERISTICS:
    ( A ) LENGTH: 12
    ( B ) TYPE: Amino Acid
    ( C ) STRANDEDNESS: Unknown
    ( D ) TOPOLOGY: Unknown ( x i ) SEQUENCE DESCRIPTION: SEQ ID NO: 17:

Leu  Pro  Thr  Pro  Pro  Thr  Arg  Glu  Pro  Lys  Lys  Val
 1              5                          10

( 2 ) INFORMATION FOR SEQ ID NO: 18:

( i ) SEQUENCE CHARACTERISTICS:
    ( A ) LENGTH: 12
    ( B ) TYPE: Amino Acid
    ( C ) STRANDEDNESS: Unknown
    ( D ) TOPOLOGY: Unknown ( x i ) SEQUENCE DESCRIPTION: SEQ ID NO: 18:

Pro  Thr  Pro  Pro  Thr  Arg  Glu  Pro  Lys  Lys  Val  Ala
 1              5                          10

( 2 ) INFORMATION FOR SEQ ID NO:19:

( i ) SEQUENCE CHARACTERISTICS:
    ( A ) LENGTH: 12
    ( B ) TYPE: Amino Acid
    ( C ) STRANDEDNESS: Unknown
    ( D ) TOPOLOGY: Unknown ( x i ) SEQUENCE DESCRIPTION: SEQ ID NO: 19:

Thr  Pro  Pro  Thr  Arg  Glu  Pro  Lys  Lys  Val  Ala  Val
 1              5                          10

( 2 ) INFORMATION FOR SEQ ID NO: 20:

( i ) SEQUENCE CHARACTERISTICS:
    ( A ) LENGTH: 12
    ( B ) TYPE: Amino Acid
    ( C ) STRANDEDNESS: Unknown
    ( D ) TOPOLOGY: Unknown ( x i ) SEQUENCE DESCRIPTION: SEQ ID NO: 20:

Pro  Pro  Thr  Arg  Glu  Pro  Lys  Lys  Val  Ala  Val  Val
 1              5                          10

( 2 ) INFORMATION FOR SEQ ID NO: 21:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 21:

```
Pro  Thr  Arg  Glu  Pro  Lys  Lys  Val  Ala  Val  Val  Arg
 1              5                        10
```

( 2 ) INFORMATION FOR SEQ ID NO: 22:

( i ) SEQUENCE CHARACTERISTICS:
        ( A ) LENGTH: 12
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 22:

```
Thr  Arg  Glu  Pro  Lys  Lys  Val  Ala  Val  Val  Arg  Thr
 1              5                        10
```

( 2 ) INFORMATION FOR SEQ ID NO: 23:

( i ) SEQUENCE CHARACTERISTICS:
        ( A ) LENGTH: 391
        ( B ) TYPE: Amino Acid
        ( C ) STRANDEDNESS: Unknown
        ( D ) TOPOLOGY: Unknown ( x i ) SEQUENCE DESCRIPTION: SEQ ID NO: 23:

```
Met  Val  Arg  Ser  Ser  Ser  Gln  Asn  Ser  Ser  Asp  Lys  Pro
 1              5                        10

Val  Ala  His  Val  Val  Ala  Asn  His  Gln  Val  Glu  Glu  Gln
          15                  20                        25

Gly  Ile  His  His  His  His  His  His  Val  Asp  Pro  Gly  Pro
               30                       35

Met  Ala  Glu  Pro  Arg  Gln  Glu  Phe  Glu  Val  Met  Glu  Asp
 40                       45                       50

His  Ala  Gly  Thr  Tyr  Gly  Leu  Gly  Asp  Arg  Lys  Asp  Gln
          55                       60                       65

Gly  Gly  Tyr  Thr  Met  His  Gln  Asp  Gln  Glu  Gly  Asp  Thr
                    70                       75

Asp  Ala  Gly  Leu  Lys  Ala  Glu  Glu  Ala  Gly  Ile  Gly  Asp
          80                  85                       90

Thr  Pro  Ser  Leu  Glu  Asp  Glu  Ala  Ala  Gly  His  Val  Thr
                95                       100

Gln  Ala  Arg  Met  Val  Ser  Lys  Ser  Lys  Asp  Gly  Thr  Gly
105                      110                      115

Ser  Asp  Asp  Lys  Lys  Ala  Lys  Gly  Ala  Asp  Gly  Lys  Thr
               120                 125                      130

Lys  Ile  Ala  Thr  Pro  Arg  Gly  Ala  Ala  Pro  Pro  Gly  Gln
                    135                      140

Lys  Gly  Gln  Ala  Asn  Ala  Thr  Arg  Ile  Pro  Ala  Lys  Thr
          145                      150                      155

Pro  Pro  Ala  Pro  Lys  Thr  Pro  Pro  Ser  Ser  Gly  Glu  Pro
                    160                      165
```

| Pro | Lys | Ser | Gly | Asp | Arg | Ser | Gly | Tyr | Ser | Ser | Pro | Gly |
| 170 | | | | 175 | | | | 180 | | | | |

| Ser | Pro | Gly | Thr | Pro | Gly | Ser | Arg | Ser | Arg | Thr | Pro | Ser |
| | | 185 | | | | 190 | | | | | 195 | |

| Leu | Pro | Thr | Pro | Pro | Thr | Arg | Glu | Pro | Lys | Val | Ala |
| | | | 200 | | | | 205 | | | | |

| Val | Val | Arg | Thr | Pro | Pro | Lys | Ser | Pro | Ser | Ser | Ala | Lys |
| 210 | | | | | 215 | | | | | 220 | | |

| Ser | Arg | Leu | Gln | Thr | Ala | Pro | Val | Pro | Met | Pro | Asp | Leu |
| | | | 225 | | | | | 230 | | | | |

| Lys | Asn | Val | Lys | Ser | Lys | Ile | Gly | Ser | Thr | Glu | Asn | Leu |
| 235 | | | | | 240 | | | | 245 | | | |

| Lys | His | Gln | Pro | Gly | Gly | Gly | Lys | Val | Gln | Ile | Val | Tyr |
| | | 250 | | | | | 255 | | | | 260 | |

| Lys | Pro | Val | Asp | Leu | Ser | Lys | Val | Thr | Ser | Lys | Cys | Gly |
| | | | | 265 | | | | | 270 | | | |

| Ser | Leu | Gly | Asn | Ile | His | His | Lys | Pro | Gly | Gly | Gly | Gln |
| 275 | | | | | | 280 | | | | | 285 | |

| Val | Glu | Val | Lys | Ser | Glu | Lys | Leu | Asp | Phe | Lys | Asp | Arg |
| | | | 290 | | | | | 295 | | | | |

| Val | Gln | Ser | Lys | Ile | Gly | Ser | Leu | Asp | Asn | Ile | Thr | His |
| 300 | | | | | 305 | | | | | 310 | | |

| Val | Pro | Gly | Gly | Gly | Asn | Lys | Lys | Ile | Glu | Thr | His | Lys |
| | | 315 | | | | | 320 | | | | | 325 |

| Leu | Thr | Phe | Arg | Glu | Asn | Ala | Lys | Ala | Lys | Thr | Asp | His |
| | | | | 330 | | | | | 335 | | | |

| Gly | Ala | Glu | Ile | Val | Tyr | Lys | Ser | Pro | Val | Val | Ser | Gly |
| | 340 | | | | | 345 | | | | | 350 | |

| Asp | Thr | Ser | Pro | Arg | His | Leu | Ser | Asn | Val | Ser | Ser | Thr |
| | | | 355 | | | | | 360 | | | | |

| Gly | Ser | Ile | Asp | Met | Val | Asp | Ser | Pro | Gln | Leu | Ala | Thr |
| 365 | | | | | 370 | | | | | 375 | | |

| Leu | Ala | Asp | Glu | Val | Ser | Ala | Ser | Leu | Ala | Lys | Gln | Gly |
| | | 380 | | | | | 385 | | | | | 390 |

Leu ( 2 ) INFORMATION FOR SEQ ID NO: 24:

( i ) SEQUENCE CHARACTERISTICS:
        ( A ) LENGTH: 1173
        ( B ) TYPE: Nucleic Acid
        ( C ) STRANDEDNESS: Double Stranded
        ( D ) TOPOLOGY: Unknown ( x i ) SEQUENCE DESCRIPTION: SEQ ID NO: 24:

| | | | | |
|---|---|---|---|---|
| ATGGTAAGAT | CAAGTAGTCA | AAATTCGAGT | GACAAGCCTG | 40 |
| TAGCCCACGT | CGTAGCAAAC | CACCAAGTGG | AGGAGCAGGG | 80 |
| AATTCACCAT | CACCATCACC | ACGTGGATCC | CGGGCCCATG | 120 |
| GCTGAGCCCC | GCCAGGAGTT | CGAAGTGATG | GAAGATCACG | 160 |
| CTGGGACGTA | CGGGTTGGGG | GACAGGAAAG | ATCAGGGGGG | 200 |
| CTACACCATG | CACCAAGACC | AAGAGGGTGA | CACGGACGCT | 240 |
| GGCCTGAAAG | CTGAAGAAGC | AGGCATTGGA | GACACCCCCA | 280 |
| GCCTGGAAGA | CGAAGCTGCT | GGTCACGTGA | CCCAAGCTCG | 320 |

| | | | | |
|---|---|---|---|---|
| CATGGTCAGT | AAAAGCAAAG | ACGGGACTGG | AAGCGATGAC | 360 |
| AAAAAAGCCA | AGGGGGCTGA | TGGTAAAACG | AAGATCGCCA | 400 |
| CACCGCGGGG | AGCAGCCCCT | CCAGGCCAGA | AGGGCCAGGC | 440 |
| CAACGCCACC | AGGATTCCAG | CAAAAACCCC | GCCCGCTCCA | 480 |
| AAGACACCAC | CCAGCTCTGG | TGAACCTCCA | AAATCAGGGG | 520 |
| ATCGCAGCGG | CTACAGCAGC | CCCGGCTCCC | CAGGCACTCC | 560 |
| CGGCAGCCGC | TCCCGCACCC | CGTCCCTTCC | AACCCCACCC | 600 |
| ACCCGGGAGC | CCAAGAAGGT | GGCAGTGGTC | CGTACTCCAC | 640 |
| CCAAGTCGCC | GTCTTCCGCC | AAGAGCCGCC | TGCAGACAGC | 680 |
| CCCCGTGCCC | ATGCCAGACC | TGAAGAATGT | CAAGTCCAAG | 720 |
| ATCGGCTCCA | CTGAGAACCT | GAAGCACCAG | CCGGGAGGCG | 760 |
| GGAAGGTGCA | AATAGTCTAC | AAACCAGTTG | ACCTGAGCAA | 800 |
| GGTGACCTCC | AAGTGTGGCT | CATTAGGCAA | CATCCATCAT | 840 |
| AAACCAGGAG | GTGGCCAGGT | GGAAGTAAAA | TCTGAGAAGC | 880 |
| TTGACTTCAA | GGACAGAGTC | CAGTCGAAGA | TTGGGTCCCT | 920 |
| GGACAATATC | ACCCACGTCC | CTGGCGGAGG | AAATAAAAAG | 960 |
| ATTGAAACCC | ACAAGCTGAC | CTTCCGCGAG | AACGCCAAAG | 1000 |
| CCAAGACAGA | CCACGGGGCG | GAGATCGTGT | ACAAGTCGCC | 1040 |
| AGTGGTGTCT | GGGGACACGT | CTCCACGGCA | TCTCAGCAAT | 1080 |
| GTCTCCTCCA | CCGGCAGCAT | CGACATGGTA | GACTCGCCCC | 1120 |
| AGCTCGCCAC | GCTAGCTGAC | GAGGTGTCTG | CCTCCCTGGC | 1160 |
| CAAGCAGGGT | TTG | | | 1173 |